United States Patent [19]
Dreyfuss et al.

[11] Patent Number: 5,876,949
[45] Date of Patent: Mar. 2, 1999

[54] ANTIBODIES SPECIFIC FOR FRAGILE X RELATED PROTEINS AND METHOD OF USING THE SAME

[75] Inventors: Gideon Dreyfuss, Wynnewood; Mikiko C. Siomi; Yan Zhang, both of Philadelphia, all of Pa.

[73] Assignee: The Trustees of the University of Pennsylvania, Philadelphia, Pa.

[21] Appl. No.: 455,073

[22] Filed: May 31, 1995

[51] Int. Cl.⁶ .................. G01N 33/567; C07K 16/28; C12P 21/08
[52] U.S. Cl. ............. 435/7.21; 530/387.9; 530/388.85; 530/389.1
[58] Field of Search .............. 530/387.1, 388.21, 530/388.85, 387.9, 388.7, 389.1, 389.6; 435/4, 7.21

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 4,736,866 | 4/1988 | Leder et al. . |
| 4,873,191 | 10/1989 | Wagner et al. . |
| 4,965,188 | 10/1990 | Mullis et al. . |
| 5,075,216 | 12/1991 | Innis et al. . |

FOREIGN PATENT DOCUMENTS

| | | |
|---|---|---|
| WO 86/05512 | 9/1986 | WIPO . |
| WO 90/05194 | 5/1990 | WIPO . |
| WO 91/09140 | 6/1991 | WIPO . |
| WO 92/12262 | 7/1992 | WIPO . |
| WO 92/14840 | 9/1992 | WIPO . |
| WO 92/20825 | 11/1992 | WIPO . |
| WO 93/15225 | 8/1993 | WIPO . |
| WO 94/28172 | 12/1994 | WIPO . |

OTHER PUBLICATIONS

Abitbol, M. et al., "Nucleus Basalis Magnocellularis and Hippocampus are the Major Sites of FMR–1 Expression in the Human Fetal Brain", *Nature Genetics* 1993, 4, 147–152.
Ashley, C. et al., "FMR 1 Protein: Conserved RNP Family Domains and Selective RNA Binding", *Science* 1993, 262, 563–566.
Bachner, D. et al., "Enhanced Fmr–1 Expression in Testis", *Nature Genetics* 1993, 4, 115–116.
Bakker, C. et al., "Fmr1 Knockout Mice: A model to Study Fragile X Mental Retardation", *Cell* 1994,78,23–33.
Burd, C. et al., "Conserved Structures and Diversity of Functions of RNA–binding Proteins", *Science* 1994, 265, 615–621.
Capecchi, M., "Altering the Genome by Homologous Recombination", *Science* 1989, 244, 1288–1292.
De Boulle, K. et al., "A Point Mutation in the FMR–1 Gene Associated with Fragile X Mental Retardation", *Nature Genetics* 1993, 3, 31–35.
Devys, D. et al., "The FMR–1 Protein is Cytoplasmic, Most Abundant in Neurons and Appears Normal in Carriers of a Fragile X Premutation", *Nature Genetics* 1993, 4, 335–340.

Eichler, E. et al., "Fine Structure of the Human FMR1 Gene", *Hum. Mol. Genetics* 1993, 2(8), 1147–1153.
Fu, Y.–H. et al., "Variation of the CGG Repeat at the Fragile X Site Results in Genetic Instability: Resolution of the Sherman Paradox", *Cell* 1991, 67, 1047–1058.
Gibson, T. et al., "The KH Domain Occurs in a Diverse Set of RNA–binding Proteins That INclude the Antiterminator NusA and is Probably Involved in Binding to Nucleic Acid", *FEBS Letters* 1993, 324(3), 361–366.
Gibson, T. et al., "KH Domains Within the FMR1 Sequence Suggest That Fragile X Syndrome Stems From a Defect in RNA Metabolism", *Trends Biochem. Sci.* 1993, 18, 331–333.
Green, E. and Olson, "Systematic Screening of Yeast Artificial–chromosome Libraries by Use of the Polymerase Chain Reaction", *PNAS USA* 1990, 87, 1213–1217.
Hagerman, R., "Fragile X Syndrome Diagnosis, Treatment and Research", The John Hopkins University Press, Baltimore, 1991, pp. 1–68.
Hinds, H. et al., "Tissue Specific Expression of FMR–1 Provides Evidence for a Functional Role in Fragile X Syndrome", *Nature Genetics* 1993, 3, 36–43.
Janne, P.A. et al., "Localization of the 75–kDa Inositol Polyphosphate–5–phosphatase (INPP5B) to Human Chromosome Band 1p34", *Cytogenet. Cell Genet.* 1994, 66, 164–166.
Kiledjian, M. and Dreyfuss, "Primary Structure and Binding Activity of the hnRNP U Protein: Binding RNA Through RGG Box", *The EMBO Journal* 1992, 11(7), 2655–2664.
Li, P. et al., "Mice Deficient in IL–1β–Converting Enzyme Are Defective in Production of Mature IL–1β and Resistant to Endotoxic Shock", *Cell* 1995, 80, 401–411.
Nussbaum, R. and Ledbetter, "The Fragile X Syndrome", from Metabolic Basis of Inherited Disease, Scriver, C.R. et al., eds., Johns Hopkins University Press, Baltimore, 1995, pp. 759–810.
Oberle, I. et al., "Instability of a 550–Base Pair DNA Segment and Abnormal Methylation in Fragile X Syndrome", *Science* 1991, 252, 1097–1102.

(List continued on next page.)

*Primary Examiner*—Frank C. Eisenschenk
*Assistant Examiner*—Evelyn Rabin
*Attorney, Agent, or Firm*—Woodcock Washburn Kurtz Mackiewciz & Norris LLP

[57] ABSTRACT

The present invention relates to substantially pure FXR1 and FXR2 proteins and isolated nucleic acid molecules encoding the same. Recombinant expression vectors comprising nucleic acid sequences that encode FXR1 and FXR2 protein are also provided. Antibodies which bind to an epitope of FXR1 or FXR2, or FMR1 protein are also provided. The present invention also relates to methods of screening individuals for FMR1 deficiency using antibodies or nucleic acid molecules of the invention and pharmaceutical kits for accomplishing the same.

9 Claims, 1 Drawing Sheet

OTHER PUBLICATIONS

Oostra, B. et al., "Fragile X Syndrome: A Growing Gene", in Genome Maps and Neurological Disorders, Davies and Tilghman, ed., vol. 6, Cold Spring Harbor Laboratory Press, 1993, pp. 45–75.

Pieretti, M. et al., "Absence of Expression of the FMR–1 Gene in Fragile X Syndrome", *Cell* 1991, 66, 817–822.

Siomi, H. et al., "The Protein Product of the Fragile X Gene, FMR1, Has Characteristics of an RNA–Binding Protein", *Cell* 1993, 74, 291–298.

Siomi, H. et al., "Essential Role for KH Domains in RNA Binding: Impaired RNA Binding by a Mutation in the KH Domain of FMR1 That Causes Fragile X Syndrome", *Cell* 1994, 77, 33–39.

Simoi, H. et al., "The Pre–mRNA Binding K Protein Contains a Novel Evolutionarily Conserved Motif", *Nucleic Acids Research* 1993, 21(5), 1193–1198.

Swanson, M. and Dreyfuss, "Classification and Purification of Proteins of Heterogeneous Nuclear RIbonucleoprotein Particles by RNA–Binding Specificities", *Mol. and Cell. Biology* 1988, 8(5), 2237–2241.

Verheij, C. et al., "Characterization and Localization of the FMR–1 Gene Product Associated with Fragile X Syndrome", *Nature* 1993, 363, 722–724.

Verkerk, A. et al., "Identification of a Gene (FMR–1) Containing a CGG Repeat Coincident wiht a Breakpoint Cluster Region Exhibiting Length Variation in Fragile X Syndrome", *Cell* 1991, 65, 905–914.

Wide, L., "Solid Phase Antigen–Antibody Systems", in Radioimmunoassay Methods, Kirkham, K.E. and Hunter, eds., Churchill Livingstone, Edinburgh, 1971, pp. 405–412.

Yu, S. et al., "Fragile X Genotype Characterized by an Unstable Region of DNA", *Science* 1991, 252, 1179–1181.

Annemieke, et al., "Identification of a Gene (FMR–1) Containing a CGG Repeat Coincident with a Breakpoint Cluster Region Exhibiting Length Variation in Fragile X Syndrome", *Cell* 1991, 65, 905–914.

Nishiguchi et al., "A Survey of Genes Expressed in undifferentiated Mouse Embryonal Carcinoma F9 Cells: Characterization of Low–Abundance mRN As", *J. Biochem.,* 1994, 116, 128–139.

Database EST–STS, Accession No. D21720 (submitted to DDJB on Oct. 25, 1993,) by K. Shimada.

Database EST–STS, Accession No. Z43330 (submitted of Oct. 24, 1994).

FIGURE 1

ANTIBODIES SPECIFIC FOR FRAGILE X RELATED PROTEINS AND METHOD OF USING THE SAME

FIELD OF THE INVENTION

The invention relates to novel human proteins, FXR1 and FXR2, which are related to FMR1, the protein associated with Fragile X syndrome. The invention relates to diagnostic assays for identifying individuals with Fragile X syndrome.

BACKGROUND OF THE INVENTION

Fragile X mental retardation syndrome is one of the most common human genetic diseases and the most common cause of hereditary mental retardation, affecting about 1 in 1200 males and 1 in 2500 females. Reviewed in Oostra, et al., (1993) in *Genome analysis: Gemone mapping and neurological disorder*, Vol. 6, K. E. Davies and S. M. Tilghman (Eds.), Cold Spring Harbor Laboratory Press, New York, pp. 45–75 and Nussbaum, R. L. and Ledbetter, D. H., (1995) in *Metabolic Basis of Inherited Disease*, C. R. Scriver, et al. (Eds.), McGraw Hill, New York, 7th Ed., pp. 795–810. The syndrome is characterized by mental retardation (average I.Q. of 20–60) and varying degrees of autistic behavior, macroorchidism in adult males, characteristic facial features and hyperextensible joints. Hagerman, R. J., (1991) in *Fragile X syndrome: Diagnosis, treatment, and research*, R. J. Hagerman and A. C. Silverman (Eds.), Johns Hopkins University Press, Baltimore, pp. 1–68.

The gene directly responsible for fragile X syndrome, FMR1, is located at Xq27.3. Verkerk, et al., *Cell*, 1991, 65, 905–914. The nucleotide and amino acid sequences of FMR1 are set forth in SEQ ID NO:1 and SEQ ID NO:2, respectively. The 5' untranslated region of the FMR1 gene contains a polymorphic CGG trinucleotide repeat, 6–60 repeats found in normal individuals, which can be amplified to hundreds or thousands of copies in affected patients. Verkerk, et al., *Cell*, 1991, 65, 905–914; Oberle, et al., *Science*, 1991, 252, 1097–1102; Yu, et al., *Science*, 1991, 252, 1179–1181; Fu, et al., *Cell*, 1991, 67, 1047–1058. Fragile X syndrome usually results from expansion of the CGG repeats leading to hypermethylation of the CpG island adjacent to FMR1 and loss of transcription of the FMR1 gene. Pieretti, et al., *Cell*, 1991, 66, 817–822. Indeed, affected patients usually do not have detectable FMR1 protein. Siomi, et al., *Cell*, 1993, 74, 291–298 and Verheij, et al., *Nature*, 1993, 363, 722–724. The FMR1 mRNA and protein are expressed in many tissues, but particularly high levels are found in the brain and in tubules of the testes which are two of the major organs affected in fragile X syndrome. Hinds, et al., *Nature Genet.*, 1993, 3, 36–43; Devys, et al., *Nature Genet.*, 1993, 4, 335–340; Abitbol, et al., *Nature Genet.*, 1993, 4, 147–152; and Bachner, et al., *Nature Genet.*, 1993, 4, 115–116.

FMR1 knockout mice have been generated. These knockout mice lack normal FMR1 mRNA and protein expression and show enlarged testes, impaired cognitive function, and abnormal behavior. This animal model supports the central role of FMR1 in fragile X syndrome and it may serve as a valuable tool for the elucidation of the physiological role of FMR1. Bakker, et al., *Cell*, 1994, 78, 23–33.

The FMR1 protein contains motifs characteristic of RNA-binding proteins, namely two KH domains and an RGG box (Siomi, et al., *Cell*, 1993, 74, 291–298; Ashley, et al., *Science*, 1993, 262, 563–566; and Gibson, et al., *Trends Biochem. Sci.*, 1993, 18, 331–333), and has been shown to bind RNA in vitro (Siomi, et al., *Cell*, 1993, 74, 291–298; and Ashley, et al., *Science*, 1993, 262, 563–566). Importantly, the RNA-binding activity of the FMR1 Ile-304→Asn mutant (which changes a highly conserved residue in the KH domain) that was found in a patient with severe fragile X syndrome (De Boulle, et al., *Nature Genet.*, 1993, 3, 31–35), is impaired (Siomi, et al., *Cell*, 1994, 77, 33–39). Together, these findings suggest a strong connection between fragile X syndrome and the RNA-binding activity of FMR1. However, the cognate RNA target of FMR1 and its precise functions have not yet been elucidated.

PCT Publication WO 90/05194, which is incorporated herein by reference, describes a probe that is used to detect fragile X syndrome. The probe consists of a nucleic acid fragment that is hybridizable with the human X chromosome at the region Xq27.3-DXS52.

PCT Publication WO 91/09140, which is incorporated herein by reference, describes a probe for the detection of fragile X syndrome. The probe comprises at least 17 contiguous nucleotide bases.

PCT Publication WO 92/20825, which is incorporated herein by reference, describes nucleotide sequences and cosmids used to detect fragile X syndrome. The nucleotide sequences correspond to the FMR-1 gene.

PCT Publication WO 86/05512, which is incorporated herein by reference, describes DNA probes that recognize the polymorphic locus of the q28 region of the X chromosome.

PCT Publication WO 93/15225, which is incorporated herein by reference, describes a method of amplifying and detecting specific GC-rich nucleic acid sequences by polymerase chain reaction (PCR), which may be used to detect individuals with fragile X syndrome. The method determines whether the number of CGG repeats in the test individual's X-chromosome are characteristic of a normal, carrier, or afflicted person. Such a method is used to amplify and detect the GC-rich region of the FMR1 gene.

PCT Publication WO 92/12262, which is incorporated herein by reference, describes DNA sequences that may be used to detect individuals with fragile X syndrome. The DNA sequences span the fragile X site on the human X chromosome.

PCT Publication WO 92/14840, which is incorporated herein by reference, describes nucleic acid fragments containing mutations associated with the fragile X syndrome that may be used to detect individuals with mental retardation.

There remains a need for reagents, kits and methods useful in the identification of individuals suffering from fragile X syndrome. There is a need for reagents, kits and methods useful in the identification of individuals suffering from FMR1 deficiency without misdiagnosing an individual's condition due to cross-reactivity with fragile X related proteins.

SUMMARY OF THE INVENTION

The present invention relates to substantially pure FXR1 protein.

The present invention relates to nucleic acid molecules that encode FXR1 protein.

The present invention relates to recombinant expression vectors that comprise a nucleic acid sequence that encodes FXR1 protein.

The present invention relates to host cells that comprise recombinant expression vectors that encode FXR1 protein.

The present invention relates to fragments of nucleic acid molecules with sequences encoding FXR1 protein that have at least 10 nucleotides.

The present invention relates to oligonucleotide molecules that comprise a nucleotide sequence complimentary to a nucleotide sequence of at least 10 nucleotides of SEQ ID NO:3.

The present invention relates to substantially pure FXR2 protein.

The present invention relates to nucleic acid molecules that encode FXR2 protein.

The present invention relates to nucleic acid molecules encoding FXR2 protein that consists of SEQ ID NO:5.

The present invention relates to recombinant expression vectors that comprise a nucleic acid sequence that encodes FXR2 protein.

The present invention relates to host cells that comprise recombinant expression vectors that encode FXR2 protein.

The present invention relates to fragments of nucleic acid molecules with sequences encoding FXR2 protein that have at least 10 nucleotides.

The present invention relates to oligonucleotide molecules that comprise a nucleotide sequence complimentary to a nucleotide sequence of at least 10 nucleotides of SEQ ID NO:5.

The present invention relates to isolated antibodies which bind to an epitope on SEQ ID NO:4.

The present invention relates to isolated antibodies which bind to an epitope on SEQ ID NO:6.

The present invention relates to isolated antibodies which bind to FMR1 protein but not FXR1 protein or FXR2 protein.

The present invention relates to methods of screening individuals for FMR1 deficiency comprising the steps of contacting a sample of tissue or body fluid from said individual with antibodies that bind to FMR1 but not to FXR1 or FXR2 and detecting the FMR1-specific antibodies that are bound to FMR1 in the sample.

The present invention relates to methods of screening individuals for FMR1 deficiency comprising the steps of contacting a sample of nucleic acid molecules derived from tissue or body fluid from the individual with nucleic acid molecules that hybridize to nucleotide sequences that encode FMR1 but not FXR1 or FXR2.

The present invention relates to methods of screening individuals for FMR1 deficiency comprising the steps of amplifying nucleic acid molecules derived from tissue or body fluid from the individual using polymerase chain reaction primers that amplify nucleotide sequences that encode FMR1 but not FXR1 or FXR2.

The present invention relates to FXR1 knockout mice which lack normal FXR1 and are homozygous for a mutated, non-functional FXR1 gene.

The present invention relates to FXR2 knockout mice which lack normal FXR2 and are homozygous for a mutated, non-functional FXR2 gene.

The present invention relates to pharmaceutical kit comprising a container comprising antibodies which bind to FMR1 but not FXR1 or FXR2, positive and negative controls, and instructions.

The present invention relates to pharmaceutical kit comprising a container comprising nucleic acid molecules which hybridize to nucleic acid molecules encoding FMR1 but not FXR1 or FXR2, positive and negative controls, and instructions.

DETAILED DESCRIPTION OF THE DRAWINGS

Figure 1:
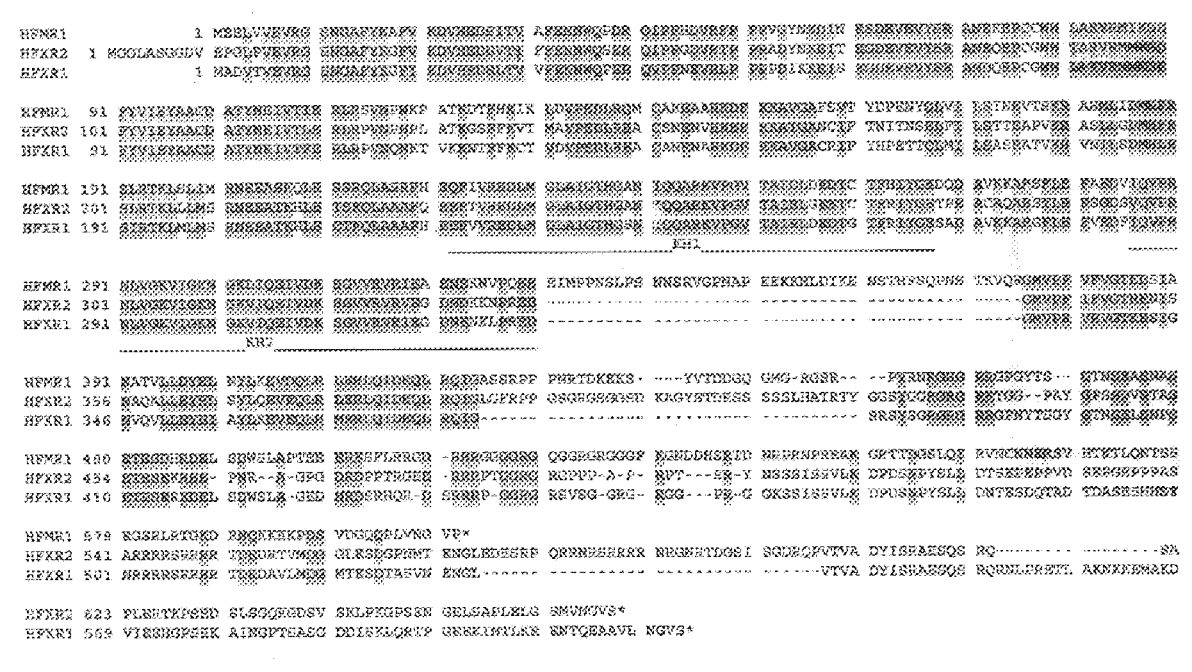

FIG. 1 shows a comparison of the amino acid sequences for human FMR1 (SEQ ID NO:2), FXR1 (SEQ ID NO:4) and FXR2 (SEQ ID NO:6). Conserved amino acids among the three proteins are shaded. The dashes indicate the placement of gaps to maximize alignment between the sequences. The amino acid position is shown at the left.

DETAILED DESCRIPTION OF THE INVENTION

Two novel human genes, termed FXR1 and FXR2, that are highly homologous by amino acid sequence to FMR1 have been discovered. The FXR1 and FXR2 proteins are cytoplasmic RNA-binding proteins that are expressed in many tissues. However, unlike FMR1, neither FXR1 nor FXR2 are located on the X chromosome. FXR1 is an autosomal gene located at 12q13. FXR2 is an autosomal gene located at 17p13.1.

According to some methods of detecting individuals with mental retardation caused by conditions such as fragile X syndrome, large nucleotide sequences, such as cosmids, are used to detect various loci associated with fragile X syndrome. After FMR1 was isolated, subsequent approaches used nucleotide probes to detect the GC-rich region in the 5'-UTR of the FMR1 gene. In addition, immunoassays have been proposed to identify individuals who are suffering from FMR1 deficiencies.

Two new genes, FXR1 and FXR2, have now been discovered that have significant sequence homology with FMR1. Thus, any nucleotide probes or antibodies used to detect the FMR1 gene or FMR1 protein, respectively, may cross-react with FXR1 or FXR2 genes and proteins. The detection of FXR1 or FXR2 may lead to the belief that the FMR1 gene or protein has been detected, resulting in a misdiagnosis. The present invention overcomes this problem by providing the means to detect unique FMR1 nucleotide or amino acid sequences which do not cross react with corresponding regions of the FXR1 and FXR2 genes and proteins.

The present invention provides the cloned gene that encodes FXR1. The nucleotide sequence that encodes FXR1 and that is disclosed herein as SEQ ID NO:3 allows for the production of pure FXR1 and the design of probes which specifically hybridize to nucleic acid molecules that encode FXR1 and antisense compounds to inhibit transcription of the gene that encodes FXR1.

The present invention provides the cloned gene that encodes FXR2. The nucleotide sequence that encodes FXR2 and that is disclosed herein as SEQ ID NO:5 allows for the production of pure FXR2 and the design of probes which specifically hybridize to nucleic acid molecules that encode FXR2 and antisense compounds to inhibit transcription of the gene that encodes FXR2.

Antibodies that specifically bind to FXR1 are provided. Such antibodies are may be used in methods of isolating pure FXR1. In some preferred embodiments, the antibodies do not cross react with FMR1 and can be used to distinguish FXR1 from FMR1. Such antibodies may, for example, bind to an epitope within amino acids 380 to 621 or 535 to 621 of FXR1 (as found in SEQ ID NO:4). In some preferred embodiments, the antibodies do not cross react with FXR2 and can be used to distinguish FXR1 from FXR2. In some preferred embodiments, the antibodies do not cross react with FMR1 and FXR2 and can be used to distinguish FXR1 from FMR1 and FXR2.

Antibodies that specifically bind to FXR2 are provided. Such antibodies may be used in methods of isolating pure FXR2. In some preferred embodiments, the antibodies do not cross react with FMR1 and can be used to distinguish FXR2 from FMR1. Such antibodies may, for example, bind to an epitope within amino acids 390 to 673 or 574 to 673 of FXR2 (as found in SEQ ID NO:6). In some preferred embodiments, the antibodies do not cross react with FXR1 and can be used to distinguish FXR2 from FXR1. In some preferred embodiments, the antibodies do not cross react with FMR1 and FXR1 and can be used to distinguish FXR2 from FMR1 and FXR1.

Antibodies that specifically bind to FMR1 are provided. Such antibodies may be used in methods of isolating pure FMR1. Such antibodies are may be used in methods of identifying individuals who have fragile X syndrome. That is, by identifying individuals whose tissue shows an absence or deficiency in FMR1, a diagnosis of fragile X syndrome is indicated. In some preferred embodiments, the antibodies do not cross react with FXR1 or FXR2 and can be used to distinguish FMR1 from FXR1 and FXR2, thereby eliminating false positive and misdiagnosis.

The present invention provides substantially purified FXR1 and FXR2 which have amino acid sequences consisting of SEQ ID NO:4 and SEQ ID NO:6, respectively. The amino acid and nucleotide sequences for FXR1 and FXR2 may vary according to the clone from which they were isolated. It is expected that amino acid substitutions or deletions may be found in proteins isolated from numerous clones. FXR1 and FXR2 can be isolated from natural sources, produced by recombinant DNA methods or synthesized by standard protein synthesis techniques.

Antibodies which specifically bind to a particular FXR1 or FXR2 may be used to purify the protein from natural sources using well known techniques and readily available starting materials. Such antibodies may also be used to purify the FXR1 or FXR2 from material present when producing the protein by recombinant DNA methodology. The present invention relates to antibodies that bind to FXR1 protein (SEQ ID NO:4) or FXR2 protein (SEQ ID NO:6).

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. Antibodies that bind to an epitope which is present on FXR1 or FXR2 are useful to isolate and purify the FXR1 or FXR2 from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *Antibodies: A Laboratory Manual*, Cold Spring Harbor Laboratory, Cold Spring Harbor, N.Y., which is incorporated herein by reference. Briefly, for example, FXR1 or FXR2, or an immunogenic fragment thereof, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to protein, the hybridoma which produces them is cultured to produce a continuous supply of antibodies.

Using standard techniques and readily available starting materials, nucleic acid molecules that encode FXR1 and FXR2 may each be isolated from a cDNA library, using probes which are designed based upon the nucleotide sequence information disclosed in SEQ ID NO:3 and SEQ ID NO:5, respectively. The present invention relates to an isolated nucleic acid molecule that comprises a nucleotide sequence that encodes FXR1 or FXR2 and that comprises the amino acid sequence of SEQ ID NO:4 and SEQ ID NO:6, respectively. In some embodiments, the nucleic acid molecules consist of a nucleotide sequence that encodes FXR1 or FXR2. In some embodiments, the nucleic acid molecules comprise the nucleotide sequence that consists of the coding sequence in SEQ ID NO:3 or SEQ ID NO:5. In some embodiments, the nucleic acid molecules consist of the nucleotide sequence set forth in SEQ ID NO:3 or SEQ ID NO:5. The isolated nucleic acid molecules of the invention are useful to prepare constructs and recombinant expression systems for preparing FXR1 and FXR2.

A cDNA library may be generated by well known techniques. A cDNA clone which contains one of the nucleotide sequences set out is identified using probes that comprise at least a portion of the nucleotide sequence disclosed in SEQ ID NO:3 or SEQ ID NO:5. The probes generally have at least 16 nucleotides, preferably 24 nucleotides. The probes are used to screen the cDNA library using standard hybridization techniques. Alternatively, genomic clones may be isolated using genomic DNA from any human cell as a starting material. The present invention relates to isolated nucleic acid molecules that comprise a nucleotide sequence identical or complementary to a fragment of SEQ ID NO:3 or SEQ ID NO:5 which is at least 10 nucleotides. In some embodiments, the isolated nucleic acid molecules consist of a nucleotide sequence identical or complementary to a fragment of SEQ ID NO:3 or SEQ ID NO:5 which is at least 10 nucleotides. In some embodiments, the isolated nucleic acid molecules comprise or consist of a nucleotide sequence identical or complementary to a fragment of SEQ ID NO:3 or SEQ ID NO:5 which is 15–150 nucleotides. In some embodiments, the isolated nucleic acid molecules comprise or consist of a nucleotide sequence identical or complementary to a fragment of SEQ ID NO:3 or SEQ ID NO:5 which is 15–30 nucleotides. Isolated nucleic acid molecules that comprise or consist of a nucleotide sequence identical or complementary to a fragment of SEQ ID NO:3 or SEQ ID NO:5 which is at least 10 nucleotides are useful as probes for identifying genes and cDNA sequence having SEQ ID NO:3 or SEQ ID NO:5, respectively, and PCR primers for amplifying genes and cDNA having SEQ ID NO:3 or SEQ ID NO:5, respectively.

The cDNA that encodes FXR1 and FXR2 may be used as a molecular marker in electrophoresis assays in which cDNA from a sample is separated on an electrophoresis gel and probes are used to identify bands which hybridize to such probes. Specifically, SEQ ID NO:3 or portions thereof, and SEQ ID NO:5 or portions thereof, may be used as a molecular marker in electrophoresis assays in which cDNA from a sample is separated on an electrophoresis gel and specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes FXR1 and FXR2, respectively. Electrophoresis gels useful in such an assay include standard polyacrylamide gels as described in Sambrook et al., *Molecular Cloning a Laboratory Manual*, (1989) Second Ed., Cold Spring Harbor Press, New York, which is incorporated herein by reference.

The nucleotide sequences in SEQ ID NO:3 and SEQ ID NO:5, may be used to design probes, primers and complimentary molecules which specifically hybridize to the unique nucleotide sequences of FXR1 and FXR2, respectively. Probes, primers and complimentary molecules which specifically hybridize to nucleotide sequence that encodes FXR1 and FXR2 may be designed routinely by those having ordinary skill in the art.

The present invention also includes labelled oligonucleotides which are useful as probes for performing oligonucleotide hybridization methods to identify FXR1 and FXR2. Accordingly, the present invention includes probes that can be labelled and hybridized to unique nucleotide sequences that encode FXR1 and FXR2, respectively. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of FXR1 and FXR2.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% G+C composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encodes FXR1 and FXR2 and insert it into an expression vector using standard techniques and readily available starting materials.

The present invention relates to a recombinant expression vector that comprises a nucleotide sequence that encodes FXR1 or FXR2 that comprises the amino acid sequence of SEQ ID NO:4 or SEQ ID NO:6, respectively. As used herein, the term "recombinant expression vector" is meant to refer to a plasmid, phage, viral particle or other vector which, when introduced into an appropriate host, contains the necessary genetic elements to direct expression of the coding sequence that encodes FXR1 or FXR2. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:3 or SEQ ID NO:5. The recombinant expression vectors of the invention are useful for transforming hosts to prepare recombinant expression systems for preparing FXR1 or FXR2.

The present invention relates to a host cell that comprises the recombinant expression vector that includes a nucleotide sequence that encodes FXR1 or FXR2 that comprises SEQ ID NO:4 or SEQ ID NO:6. In some embodiments, the host cell comprises a recombinant expression vector that comprises SEQ ID NO:3 or SEQ ID NO:5. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the FXR1 or FXR2 that comprises the amino acid sequence of SEQ ID NO:4 or SEQ ID NO:6. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes the invention is operably linked to a mammary cell specific promoter whereby the coding sequence is only expressed in mammary cells and the recombinant protein so expressed is recovered from the animal's milk. In some embodiments, the coding sequence that encodes an FXR1 or FXR2 is SEQ ID NO:3 or SEQ ID NO:5.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as CHO cells. One having ordinary skill in the art can use these commercial expression vectors and systems or others to produce FXR1 and FXR2 using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed., Cold Spring Harbor Press, New York (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes FXR1 or FXR2 is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate FXR1 or FXR2 that is produced using such expression systems. The methods of purifying FXR1 or FXR2 from natural sources using antibodies which specifically bind to FXR1 or FXR2 as described above, may be equally applied to purifying FXR1 or FXR2 produced by recombinant DNA methodology.

Examples of genetic constructs include the FXR1 or FXR2 coding sequences operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes FXR1 or FXR2 from readily available starting materials. Such gene constructs are useful for the production of FXR1 or FXR2.

In some embodiments of the invention, transgenic non-human animals are generated. The transgenic animals according to some embodiments of the invention contain SEQ ID NO:3 or SEQ ID NO:5 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce FXR1 or FXR2. Preferred animals are rodents, particularly goats, rats and mice.

In addition to producing these proteins by recombinant techniques, automated peptide synthesizers may also be employed to produce FXR1 and FXR2. Such techniques are well known to those having ordinary skill in the art and are useful if derivatives which have substitutions not provided for in DNA-encoded protein production.

Another aspect of the present invention relates to knock-out mice and methods of using the same. In particular, transgenic mice may be generated which are homozygous for either a mutated, non-functional FXR1 or FXR2 gene which is introduced into them using well known techniques. The mice produce no functional FXR1 or FXR2 and are useful to study the function of FXR1 or FXR2. Furthermore, the mice may be used in assays to study the effect of test compounds on FXR1 or FXR2 deficiency.

Methods of generating genetically deficient "knock out" mice are well known and disclosed in Capecchi, M. R., *Science,* 1989, 244, 1288–1292 and Li, P., et al., *Cell,* 1995, 80, 401–411, which are each incorporated herein by reference. The murine FXR1 or FXR2 genomic clone can be isolated using the homologous human sequences described herein. The genomic clone can be used to prepare a FXR1 or FXR2 targeting construct which can disrupt the FXR1 or FXR2 gene in the mouse by homologous recombination.

The targeting construct contains a non-functioning portion of the FXR1 or FXR2 gene which inserts in place of the functioning portion of the native mouse gene. The non-functioning insert generally contains an insertion in the exon that encodes the active region of FXR1 or FXR2. The targeting construct can contain markers for both positive and negative selection. The positive selection marker allows for the selective elimination of cells without it while the negative selection marker allows for the elimination of cells that carry it.

For example, a first selectable marker is a positive marker that will allow for the survival of cells carrying it. In some embodiments, the first selectable marker is an antibiotic resistance gene such as the neomycin resistance gene can be placed within the coding sequences of the FXR1 or FXR2 gene to render it non-functional while additionally rendering the construct selectable. The antibiotic resistance gene is within the homologous region which can recombine with native sequences. Thus, upon homologous reconstruction, the non-functional and antibiotic resistance selectable gene sequences will be taken up.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gancyclovir.

Cells are transfected with targeting constructs and then selected for the presence of the first selection marker and the absence of the second. Clones are then injected into the blastocysts and implanted into pseudopregnant females. Chimeric offspring which are capable of transferring the recombinant genes in their germline are selected, mated and their offspring is examined for heterozygous carriers of the recombined genes. Mating of the heterozygous offspring can then be used to generate fully homozygous offspring which are the FXR1-deficient or FXR2-deficient knockout mouse.

The present invention provides the means and methodology for accurately identifying individuals who have FMR1 deficiency, also referred to as fragile X syndrome. The discovery of two significantly related proteins, FXR1 and FXR2 and the genes that encode these proteins, allows for the more accurate detection of FMR1 protein and FMR1 gene sequences. In particular, reagents may be designed to which do not cross react with the related proteins and mRNA sequences thereby more accurately detecting the presence of FMR1 protein or mRNA.

In addition, the present invention provides the means and methodology for accurately identifying individuals who have FXR1 or FXR2 deficiencies. Reagents may be designed to detect FXR1 protein or mRNA which does not cross react with the FMR1 or FXR2 proteins and mRNA sequences, thereby allowing for more accurate detection of the presence of FXR1 protein or mRNA. Likewise, reagents may be designed to detect FXR2 protein or mRNA which does not cross react with the FMR1 or FXR1 proteins and mRNA sequences, thereby allowing for more accurate detection of the presence of FXR2 protein or mRNA.

According to some embodiments, diagnostic reagents and kits are provided for performing immunoassays to determine the presence or absence of FMR1 protein in a sample from an individual. Antibodies that bind to FMR1 but that do not bind to FXR1 and FXR2 are provided. Kits may additionally include one or more of the following: means for detecting antibodies bound to FMR1 present in a sample, instructions for performing the method, and diagrams or photographs that are representative of how positive and/or negative results appear. In addition, kits may comprise optional positive controls such as FMR1 protein. Further, optional negative controls may be provided.

Antibodies that bind to FMR1 but that do not cross react with FXR1 and FXR2 preferably bind to an epitope in the C-terminal region of FMR1. FIG. 1 depicts a comparison of the amino acid sequences of human FMR1, FXR1, and FXR2. It is preferred that antibodies of the invention bind to epitopes not shared between FMR1 and FXR1 or FMR1 and FXR2. Preferably, the antibodies bind to an epitope within the C-terminal 200 amino acids of FMR1. More preferably, the antibodies bind to an epitope within the C-terminal 100 amino acids of FMR1. Most preferably, the antibodies bind to an epitope within the C-terminal 60 amino acids of FMR1. For example, antibodies which bind to amino acids 331 to 375 or 520 to 610 of FMR1 (as found in SEQ ID NO:2) are unlikely to cross-react with either FXR1 or FXR2. One skilled in the art will readily be able to produce antibodies to FMR1 that do not cross-react with either FXR1 or FXR2.

Immunoassay methods may be used to identify individuals with fragile X syndrome by detecting the absence or deficiency of FMR1 in sample of tissue or body fluid using antibodies which bind to FMR1 but which are non-cross reactive to FXR1 and FXR2. The antibodies are preferably monoclonal antibodies. The antibodies are preferably raised against FMR1 made in human cells. The antibodies preferably bind to an epitope on FMR1 which is not present on FXR1 or FXR2. Immunoassays are well known and there design may be routinely undertaken by those having ordinary skill in the art. Those having ordinary skill in the art can produce monoclonal antibodies which specifically bind to FMR1 and which do not bind to FXR1 and FXR2 useful in methods and kits of the invention using standard techniques and readily available starting materials. The techniques for producing monoclonal antibodies are outlined in Harlow, E. and D. Lane (1988) *Antibodies: A Laboratory Manual*, Cold Spring Harbor Laboratory, Cold Spring Harbor, N.Y., which is incorporated herein by reference, provide detailed guidance for the production of hybridomas and monoclonal antibodies which specifically bind to FMR1.

According to some embodiments, immunoassays comprise allowing proteins in the sample to bind a solid phase support such as a plastic surface. Detectable antibodies are then added which selectively binding to FMR1. Detection of the detectable antibody indicates the presence of FMR1. The detectable antibody may be a labelled or an unlabelled antibody. Unlabelled antibody may be detected using a second, labelled antibody that specifically binds to the first antibody or a second, unlabelled antibody which can be detected using labelled protein A, a protein that complexes with antibodies. Various immunoassay procedures are described in Immunoassays for the 80's, Voller, et al., Ed., University Park, 1981, which is incorporated herein by reference.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, (1970) Kirkham, Ed., E. & S. Livingstone, Edinburgh, pp. 199–206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of FMR1 in a test sample is anti-FMR1 antibody. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of FMR1, detectable anti-FMR1 antibodies are used. Several methods are well known for the detection of antibodies.

One method in which the antibodies can be detectably labelled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labelled is through radioactive isotopes and subsequent use in a radioimmunoassay (RIA) (see, for example, Work, et al., Laboratory Techniques and Biochemistry in *Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3H$, $^{125}I$, $^{131}I$, $^{35}S$, and $^{14}C$. Preferably $^{125}I$ is the isotope. One skilled in the art would readily recognize other radioisotopes which may also be used.

It is also possible to label the antibody with a fluorescent compound. When the fluorescent-labelled antibody is exposed to light of the proper wavelength, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labelled using fluorescence-emitting metals such as $^{152}Eu$, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibodies can also be detectably labelled by coupling to a chemiluminescent compound. The presence of the chemiluminescent-labelled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of FMR1 and no FMR1, respectively, are added to assays being performed in parallel with the test assay. One skilled in the art would have the necessary knowledge to perform the appropriate controls.

FMR1 may be produced as a reagent for positive controls routinely. One skilled in the art would appreciate the different manners in which the FMR1 may be produced and isolated.

An "antibody composition" refers to the antibody or antibodies required for the detection of the protein. For example, the antibody composition used for the detection of FMR1 in a test sample comprises a first antibody which binds FMR1, but not FXR1 or FXR2, as well as a second or third detectable antibody that binds the first or second antibody, respectively.

To examine a test sample for the presence or absence of FMR1, a standard immunometric assay such as the one described herein may be performed. A first anti-FMR1 antibody, which recognizes a specific portion of FMR1 but not FXR1 or FXR2 is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from non-specifically binding the microtiter plate. Test sample are subsequently added to the wells and the plate is incubated for a period of time sufficient for binding to occur. The wells are washed with PBS to remove unbound protein. Labelled anti-FMR1 antibodies, which recognize portions of FMR1 not recognized by the first antibody, are added to the wells. The plate is incubated for a period of time sufficient for binding to occur and subsequently washed with PBS to remove unbound, labelled anti-FMR1 antibody. The amount of labelled and bound anti-FMR1 antibody is subsequently determined by standard techniques.

Kits which are useful for the detection of FMR1 in a test sample comprise a container comprising anti-FMR1 antibodies and a container or containers comprising controls. Controls include one control sample which does not contain FMR1 and/or another control sample which contained FMR1. The anti-FMR1 antibodies used in the kit are detectable such as being detectably labelled. If the detectable anti-FMR1 antibody is not labelled, it may be detected by second antibodies or protein A for example which may also be provided in some kits in separate containers. Additional components in some kits include solid support, buffer, and instructions for carrying out the assay. The immunoassay is useful for detecting FMR1 in homogenized tissue samples and body fluid samples including the plasma portion or cells in the fluid sample.

Western blots may be used in methods of identifying individuals suffering from fragile X syndrome by detecting presence of FMR1 in samples of tissue, such as for example, brain and testes. Western blots use detectable anti-FMR1 antibodies to bind to any FMR1 present in a sample and thus indicate the presence of the protein in the sample.

Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-FMR1 antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, N.Y.

Kits which are useful for the detection of FMR1 in a test sample by Western blot comprise a container comprising FMR1 antibodies and a container or containers comprising controls. Controls include one control sample which does not contain FMR1 and/or another control sample which contained FMR1. The anti-FMR1 antibodies used in the kit are detectable such as being detectably labelled. If the detectable anti-FMR1 is not labelled, it may be detected by second antibodies or protein A for example which may also be provided in some kits in separate containers. Additional components in some kits include instructions for carrying out the assay. The antibodies of the kit preferably bind to an epitope on the extracellular domain of FMR1.

The means to detect anti-FMR1 antibodies that are bound to FMR1 include the immunoassays described above.

Aspects of the present invention also include various methods of determining whether a sample contains cells that express FMR1 by sequence-based molecular analysis. Several different methods are available for doing so including those using Polymerase Chain Reaction (PCR) technology, using Northern blot technology, oligonucleotide hybridization technology, and in situ hybridization technology. According to the invention, samples are screened to determine the presence or absence of mRNA that encodes FMR1. In particular detection of FMR1 mRNA is performed using primers or probes which do not cross react with FXR1 mRNA or FXR2 mRNA.

The invention relates to oligonucleotide probes and primers used in the methods of identifying mRNA that encodes FMR1 and to diagnostic kits which comprise such components.

The mRNA sequence-based methods for determining whether a sample mRNA encoding FMR1 include but are not limited to PCR technology, Northern and Southern blot technology, in situ hybridization technology and oligonucleotide hybridization technology.

Primers and probes that detect FMR1 mRNA but that do not cross react with FXR1 mRNA and FXR2 mRNA preferably hybridize to nucleotide sequences that encode the C-terminal region of FMR1. It is preferred that the FMR1 specific probes or primers hybridize to nucleotide sequences that encode all or apart of the C-terminal 200 amino acids of FMR1. More preferably, the FMR1 specific probes or primers hybridize to nucleotide sequences that encode all or apart of the C-terminal 100 amino acids of FMR1. Most preferably, the FMR1 specific probes or primers hybridize to nucleotide sequences that encode all or apart of the C-terminal 60 amino acids of FMR1. One skilled in the art will readily be able to design primers and probes that hybridize to FMR1 mRNA sequences that do not cross-react with either FXR1 mRNA sequences or FXR2 mRNA sequences.

The methods described herein are meant to exemplify how the present invention may be practiced and are not meant to limit the scope of invention. It is contemplated that other sequence-based methodology for detecting the presence of specific mRNA that encodes FMR1 in tissue samples may be employed according to the invention.

A preferred method to detecting mRNA that encodes FMR1 in genetic material derived from tissue samples uses PCR technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990), which is incorporated herein by reference. Applications of PCR technology are disclosed in "Polymerase Chain Reaction" Erlich, H. A., et al., Eds. Cold Spring Harbor Press, Cold Spring Harbor, N.Y. (1989), which is incorporated herein by reference. U.S. Pat. No. 4,683,202, U.S. Pat. No. 4,683,195, U.S. Pat. No. 4,965,188 and U.S. Pat. No. 5,075,216, which are each incorporated herein by reference describe methods of performing PCR. PCR may be routinely practiced using Perkin Elmer Cetus GENEAMP RNA PCR kit, Part No. N808-0017.

To perform this method, RNA is extracted from cells in a sample and tested or used to make cDNA using well known methods and readily available starting materials. The mRNA or cDNA is combined with the FMR1 specific primers, free nucleotides and enzyme following standard PCR protocols. The mixture undergoes a series of temperature changes. If the mRNA or cDNA encoding FMR1 is present, that is, if both primers hybridize to sequences on the same molecule, the molecule comprising the primers and the intervening complementary sequences will be exponentially amplified. The amplified DNA can be easily detected by a variety of well known means. If the FMR1 encoding mRNA is not present, no DNA molecule will be exponentially amplified. The PCR technology therefore provides an extremely easy, straightforward and reliable method of detecting mRNA encoding FMR1 protein in a sample.

PCR primers can be designed routinely by those having ordinary skill in the art using well known cDNA sequence information. Primers are generally 8–50 nucleotides, preferably 18–28 nucleotides. A set of primers contains two primers. When performing PCR on extracted mRNA or cDNA generated therefrom, if the mRNA or cDNA encoding FMR1 protein is present, multiple copies of the mRNA or cDNA will be made. If it is not present, PCR will not generate a discrete detectable product.

PCR product, i.e. amplified DNA, may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotide which are useful as primers for performing PCR methods to amplify mRNA or cDNA that encodes FMR1 protein. According to the invention, diagnostic kits can be assembled which are useful to practice methods of detecting the presence of mRNA or cDNA that encodes FMR1 in tissue samples. Such diagnostic kits comprise oligonucleotide which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the mRNA or cDNA encoding FMR1.

Another method of determining whether a sample contains cells expressing FMR1 is by Northern blot analysis of mRNA extracted from a tissue sample. The techniques for performing Northern blot analyses are well known by those having ordinary skill in the art and are described in Sambrook, J. et al., *Molecular Cloning: A Laboratory Manual*, (1989) Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

One having ordinary skill in the art, performing routine techniques, could design probes to identify mRNA encoding FMR1 using the information in SEQ ID NO:1. Such probes preferentially do not cross-react with FXR1 or FXR2. The mRNA is extracted using poly dT columns and the material is separated by electrophoresis and, for example, transferred to nitrocellulose paper. Labelled probes made from an isolated specific fragment or fragments can be used to visualize the presence of a complementary fragment fixed to the paper.

According to the invention, diagnostic kits can be assembled which are useful to practice methods of detecting the presence of mRNA that encodes FMR1 in tissue samples by Northern blot analysis. Such diagnostic kits comprise oligonucleotide which are useful as probes for hybridizing to the mRNA. The probes may be radiolabelled. It is preferred that diagnostic kits according to the present invention comprise a container comprising a size marker to be run as a standard on a gel. It is preferred that diagnostic kits according to the present invention comprise a container comprising a positive control which will hybridize to the probe.

Another method of detecting the presence of mRNA encoding FMR1 protein is by oligonucleotide hybridization technology. Oligonucleotide hybridization technology is well known to those having ordinary skill in the art. Briefly, detectable probes which contain a specific nucleotide sequence that will hybridize to nucleotide sequence of mRNA encoding FMR1 protein. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences. One having ordinary skill in the art, using the sequence information disclosed in SEQ ID NO:1 can design probes which are fully complementary to mRNA sequences but not genomic DNA sequences. Such probes preferentially do not cross-react with FXR1 or FXR2. Hybridization conditions can be routinely optimized to minimize background signal by non-fully complementary hybridization.

The present invention includes labelled oligonucleotide which are useful as probes for performing oligonucleotide hybridization. That is, they are fully complementary with mRNA sequences but not genomic sequences. For example, the mRNA sequence includes portions encoded by different exons. The labelled probes of the present invention are labelled with radiolabelled nucleotides or are otherwise detectable by readily available nonradioactive detection systems.

According to the invention, diagnostic kits can be assembled which are useful to practice oligonucleotide hybridization methods of the invention. Such diagnostic kits comprise a labelled oligonucleotide which encodes portions of FMR1 encoded by different exons. It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

Another aspect of the invention relates to methods of analyzing tissue samples which are fixed sections routinely prepared by surgical pathologists to characterize and evaluate cells. In some embodiments, the cells are from brain tissue or testicular tissue and are analyzed to determine and evaluate the extent of FMR1 expression.

The present invention relates to in vitro kits for evaluating tissues samples to determine the level of FMR1 expression and to reagents and compositions useful to practice the same. The tissue is analyzed to identify the presence or absence of the FMR1 protein. Techniques such as FMR1/anti-FMR1 binding assays and immunohistochemistry assays may be performed to determine whether FMR1 is absent in cells in the tissue sample which are indicative of fragile X syndrome. Alternatively, in some embodiments of the invention, tissue samples are analyzed to identify whether FMR1 protein is being expressed in cells in the tissue sample which indicate a lack of fragile X syndrome. The presence of mRNA that encodes the FMR1 protein or cDNA generated therefrom can be determined using techniques such as in situ hybridization, immunohistochemistry and in situ FMR1 binding assay.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them. One having ordinary skill in the art, using the sequence information in SEQ ID NO:1 can design probes useful in in situ hybridization technology to identify cells that express FMR1. Such probes are preferentially FMR1 specific probes, i.e. probes that do not cross-react with, i.e. hybridize to, FXR1-encoding nucleic acid molecules or FXR2-encoding nucleic acid molecules.

The probes a fully complementary and do not hybridize well to partially complementary sequences. For in situ hybridization according to the invention, it is preferred that the probes are detectable by fluorescence. A common procedure is to label probe with biotin-modified nucleotide and then detect with fluorescently-tagged avidin. Hence, probe does not itself have to be labelled with florescent but can be subsequently detected with florescent marker.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes portions encoded by different exons. It is preferred that labelled probes of the in situ diagnostic kits according to the present invention are labelled with a fluorescent marker.

Immunohistochemistry techniques may be used to identify and essentially stain cells with FMR1. Anti-FMR1 antibodies, such as those described above, are contacted with fixed cells and the FMR1 present in the cells reacts with the antibodies. The antibodies are detectably labelled or detected using labelled second antibody or protein A to stain the cells.

FMR1 binding assays may be performed instead of immunohistochemistry except that the cell section is first frozen, then the FMR1 binding assay is performed and then the cells are fixed.

EXAMPLES

Example 1A

Materials and Methods
1. Isolation of cDNA Clones and DNA Sequencing $10^6$ plaques of λZA.PII *Xenopus laevis* ovary cDNA library were screened to obtain FMR1 and FXR1 cDNAs using the human FMR1 full length cDNA as a probe. The Xenopus FXR1 cDNA was used as a probe to screen a λgt11 cDNA library to obtain the human FXR1 cDNA. The probe was made using the FXR1-specific region to avoid isolating other FMR1-like clones. Since no initial clones contained the entire open reading frame encoding FXR1, the same library was rescreened using one of the cDNAs encoding a more amino terminal region of FXR1 as a probe. A composite transcript was determined from the overlapping clones. In vivo excision was done to create pXF43 and pXF45 for *X. laevis* FMR1 and FXR1 respectively. Phage inserts from positive clones of human FXR1 were amplified by PCR using the λgt11 phage DNA arms according to conditions suggested by the manufacturer and were cloned into pCRII vector (Invitrogen).

To create a plasmid containing full length cDNA of human FXR1, part of the inserts were subcloned into pGEM7Z vector (Promega Biotech). The nucleotide sequence of all inserts were verified by DNA sequencing. Sanger, et al., *Proc. Natl. Acad. Sci. USA*, 1977, 74, 5463–5467. All plasmids and DNA fragments were manipulated using standard techniques. Sambrook, J. et al., *Molecular Cloning: A Laboratory Manual*, (1989) Cold Spring Harbor Laboratory Press, Cold Spring Harbor, N.Y.
2. In Vitro Transcription and Translation The plasmids pXF43 for *X. laevis* FMR1, pXF45 for *X. laevis* FXR1 and pHHSI-F27X for human FMR1 (Siomi, et al., *Cell*, 1993, 74, 291–298) were linearized at appropriate restriction sites to generate templates for in vitro RNA synthesis with T3 RNA polymerase for *X. laevis* FMR1 and FXR1 and T7 RNA polymerase for human FMR1. The resultant RNAs were translated in rabbit reticulocyte lysate in the presence of ($^{35}$S)methionine (Amersham) according to the conditions of the manufacturer (Promega Biotech).
3. RNA Binding Assays Binding of in vitro produced proteins to ribohomopolymers was carried out essentially as described in Siomi, et al., Cell, 1993, 74, 291–298. In brief, ribonucleotide homopolymer (Sigma or Pharmacia) binding reactions were carried out with an equivalent of 100,000 cpm of trichloroacetic acid-precipitable protein in a total of 0.5 ml of binding buffer (10 mM Tris-HCl (pH 7.4), 2.5 mM $MgCl_2$, 0.5% Triton X100, 2 mg/ml pepstatin, 2 mg/ml leupeptin, 0.5% aprotinin) with 250 mM NaCl concentration for 10 minutes on a rocking platform at 4° C. The beads were pelleted with a brief spin in a microfuge and washed five times with binding buffer prior to resuspension in 30 μl of SDS-PAGE loading buffer. Bound protein was eluted from the nucleic acid by boiling, resolved on a SDS-polyacrylamide (12.5%) gel, and visualized by fluorograpy.

4. Production of antisera against *X. laevis* FXR1

To raise antisera specifically to *X. laevis* FXR1, pXF45 was digested with BamHI and the 600 bp fragment encoding just the carboxy terminal region of *X. laevis* FXR1 was inserted into pET15b to create the expression vector pEXFXRI. pEXFXR1 was introduced into BL21(DE3) bacteria and the His-FXR1 peptides were induced with isopropyl-β-thiogalactopylanoside as described. Studier, et al., *Methods Enzym.*, 1990, 185, 60–89; and Rosenberg, et al., *Gene*, 1987, 56, 125–135. For purification of the fusion peptide, bacterial sonicates were applied to 2 ml His-Bind resin (Novagen) column, washed and eluted as described by the manufacturer. Antisera were raised in BALB/c mice injected with the purified recombinant His-FXR1 fusion peptides produced in *E. coli*. The anti-human FMR1 antibodies were described previously. Siomi, et al., *Cell*, 1993, 74, 291–298.

5. Western Blot Analysis

The lymphoblastoid cell lines used in this work correspond to FX24 (normal sibling of FX25) and FX25 (a patient of fragile X syndrome) described in Siomi, et al., *Cell*, 1993, 74, 291–298. Cells were grown to subconfluence, lysed in SDS-PAGE sample buffer, sonicated and then heated at 95° C. for 5 minutes. Proteins were resolved on an SDS-polyacrylamide (10%) gel and transferred to nitrocellulose. Filters were incubated in blotting solution (phosphate-buffered saline, 5% nonfat milk) for at least 30 minutes at room temperature and then incubated with primary antibody diluted at 1:400 for 1 hr at room temperature. Filter were washed three times in PBS, 0.05% Tween-20, and bound antibody was detected using the peroxidase-conjugated goat anti-mouse IgG+IgM (Jackson ImmunoResearch Laboratories). The protein bands were visualized by ECL (Amersham) after washing three times in PBS, 0.05% Tween-20.

6. Immunofluorescence microscopy

HeLa cells were grown on cover glasses to subconfluence, fixed with 2% formaldehyde in PBS and permeabilized with cold acetone. After washing with cold PBS, cells were incubated with polysera for either *X. laevis* FXR1 or human FMR1 diluted at 1:400 with 3% BSA in PBS for 1 hr at room temperature, followed by washing with cold PBS extensively. Fluorescein isothiocyanate-conjugated anti-mouse $F(ab')_2$ secondary antibody (Cappel Laboratories) was diluted 1:500 with 3% BSA in PBS, applied to the cells and incubated for 1 hr at room temperature. The localization of FMR1 and FXR1 gene products in HeLa cells were detected and pictures were taken under the microscope.

7. Chromosome mapping of human FXR1

Somatic cell hybrid panel #2 was purchased from the Coriell Institute Cell Repository. This panel consists of DNA isolated from 24 human/rodent somatic cell hybrids. All but two of the hybrid retain a single intact chromosome. Primers were designed to generate a PCR product of 161 bp from a portion of the carboxy terminal end of the FXR1 open reading frame derived from a cDNA clone isolated from a HeLa cDNA library. The primer sequences are forward-5': GATGACATTTCTAAGCTACAGC-3'(1777–1798) (SEQ ID NO:7) and reverse-5': TGTACAAGCACTATTGTAAATG-3'(1916–1937) (SEQ ID NO:8). The number in the parenthesis of the primers above were based on the numbering in SEQ ID NO:3. PCR reactions were performed according to conditions suggested by manufacturer (Perkin-Elmer Cetus) and analyzed by 6%. PAGE.

8. Reverse transcription and PCR

Oligo(dT)-selected RNAs from human brain, testis, kidney, and heart were purchased from Clontech. Oligo(dT)-selected RNAs from HeLa cells and the lymphoblastoid cells (FX24 and FX25 (Siomi, et al., *Cell*, 1993, 74, 291–298)) were manually prepared using a Dynabeads mRNA direct kit (Dynal). RNA (100 ng) was reverse transcribed using the oligo (dT) primer according to conditions suggested by the manufacturer (Stratagene). PCR reactions were done on 5 μl of each cDNA solution with the primers specifically bound to FMR1 and FXR1, namely 27XM7 and 27X31 for FMR1 (Siomi, et al., *Cell*, 1993, 74, 291–298) and XF-E and XF-B1 (XF-E, 1225–1245; XF-B1, 1906–1930, the coordinates are based on the numbering used in SEQ ID NO:3 for FXRI. The samples were resolved on an agarose gel and visualized with EtBr.

Example 1B

Fragile X Mental Retardation Syndrome, the most common cause of hereditary mental retardation, is directly associated with the FMR1 gene at Xq27.3. FMR1 encodes an RNA-binding protein and the syndrome results from lack of expression of FMR1 or expression of a mutant protein that is impaired in RNA-binding. A novel gene was discovered, FXR1, that is highly homologous to FMR1 and located on chromosome 12 at 12q13. FXR1 encodes a protein which, like FMR1, contains two KH domains and is highly conserved in vertebrates. The 3' untranslated regions (3'UTRs) of the human and *Xenopus laevis* FXR1 mRNAs are strikingly conserved (~90% identity), suggesting conservation of an important function. The KH domains of FXR1 and FMR1 are almost identical, and the two proteins have similar RNA-binding properties in vitro. However, FXR1 and FMR1 have very different carboxyl termini. FXR1 and FMR1 are expressed in many tissues and both proteins, which are cytoplasmic, can be expressed in the same cells. Interestingly, cells from a fragile X patient that do not have any detectable FMR1 express normal levels of FXR1. These findings demonstrate that FMR1 and FXR1 are members of a gene family and suggest a biological role for FXR1 that is related to that of FMR1.

The human FMR1 cDNA was used to screen a Xenopus laevis ovary cDNA library by hybridization and have isolated a clone, designated FXR1 (for FMR1 unreacting relative), is a highly related homologue. The *X. laevis* FXR1 cDNA was used in hybridization screening to isolate the human FXR1 cDNA from a HeLa cell library. The nucleotide sequence and predicted amino acid sequence of the human FXR1 is shown in SEQ ID NO:3.

FXR1 has 86% amino acid sequence identity to FMR1 in the region containing the KH domains (Siomi, et al., *Nuc. Acids Res.*, 1993, 21, 1193–1198; Siomi, et al., Cell, 1993, 74, 291–298; Siomi, et al., *Cell*, 1994, 77, 33–39; Gibson, et al., *FEBS Lett.*, 1993, 324, 361–366; and Burd, et al., *Science*, 1994, 265, 615–621) and is very similar to FMR1 over the amino terminal domain (70% identity), but FXR1 and FMR1 have entirely different carboxyl domains (6% identity). The carboxyl portion of FXR1, beginning after the region containing the RGG box (Kiledjian, et al., *EMBO J.*, 1992, 11, 2655–2664; Siomi, et al., *Cell*, 1993, 74, 291–298; and Burd, et al., *Science*, 1994, 265, 615–621) has several intriguing features. There is a nine amino acid sequence RRRRSRRRR (SEQ ID NO:11) beginning at amino acid 502 of human FXR1. This arginine-rich sequence is similar to arginine-rich motifs that constitute the RNA-binding element of several proteins including HIV Rev and Tat (reviewed in Burd, et al., *Science*, 1994, 265, 615–621). Computer data base searches also picked up similar arginine/serine-rich sequences in several RNA-binding proteins, including snRNP U1 70 kDa protein and the *D. melanogaster* splicing regulator tra. In addition, the last four amino acids of both FMR1 and FXR1 contain the tripeptide NGV. The human FMR1 clone contained a sequence (amino acids 331–396; numbering according to Verkerk, et al., *Cell*, 1991, 65, 905–914) that was not found in the *X. laevis* FMR1 or in the human and *X. laevis* FXR1. This segment (amino acids 331–396) corresponds to exons 11 and 12 of the human FMR1 gene. Eichler, et al., *Hum. Mol. Genet.*, 1993, 2, 1147–1153. The absence of these exons from FXR1 and from the *X. laevis* FMR1 cDNA is probably the result of alternative splicing. Also isolated from a HeLa library was a cDNA for a shorter form of FXR1. The shorter form diverges from the longer form beginning with amino acid 535, and contains instead the sequence GKRCD (SEQ ID NO:12) as its carboxyl terminus.

The longest FXR1 cDNA that was isolated from the library contained only 12 nucleotides upstream of the putative initiation codon for the human mRNA, and 99 nucleotides of upstream sequence for the *X. laevis* mRNA. This is insufficient to establish whether or not there are CGG (or other) repeats in the 5' UTR of FXR1 mRNAs, as there are in the FMR1 mRNAs. However, there is a striking sequence feature in the 3' UTRs of FXR1 mRNAs. The 3' UTRs of the human and *X. laevis* mRNAs are about 90% identical over the 238 nucleotides (88% overall; 93% excluding the small gaps). This is a higher degree of sequence identity than is found for the coding regions of the human and the *X. laevis* FXR1 mRNAs, and it strongly suggests conservation of an important function for the FXR1 3' UTR. By comparison, the 3' UTRs of the human and the *X. laevis* FMR1 mRNAs are only 42% identical over 280 nucleotides, in which a 73-nucleotide region is 73% identical (nucleotides 2020–2092, the coordinate is based on the numbering used in Verkerk, et al., *Cell*, 1991, 65, 905–914). Out of the 12 nucleotides of the human 5' UTR sequence available so far, 11 nucleotides are identical between the human and the *X. laevis* FXRI mRNAs.

The deduced amino acid sequence of *X. laevis* FXR1 predicted a protein of molecular mass 73 kD. Consistent with this, in vitro transcription and translation of the FXRI cDNA produced a protein that migrated by SDS-PAGE at this apparent molecular mass. FMR1 binds RNA in vitro. Siomi, et al., *Cell*, 1993, 74, 291–298; and Ashley, et al., *Science*, 1993, 262, 563–566. Since FXR1, like FMR1, contains sequence motifs characteristic of RNA-binding proteins, including KH domains, an RGG box and possibly also an arginine-rich motif, the binding of RNA by FXR1 in vitro was also examined. This property was determined by an immobilized ribohomopolymer binding assay. Briefly, human FMR1 (HFMR1), *X. laevis* FMR1 (X.FMR1), and *X. laevis* FXR1 (XFXR1) were produced by in vitro transcription-translation of pHHSI-F27X (Siomi, et al., *Cell*, 1993, 74, 291–298), pXF43 and pXF45 truncated outside the coding regions. The in vitro transcribed RNA was translated in reticulocyte lysate in the presence of ($^{35}$S) methionine. An amount equivalent to 20% of the material used for each binding reaction is shown in the lanes marked "total". In vitro produced proteins were bound to 30 μl of the indicated ribonucleotide homopolymers at 250 mM NaCl and analyzed by SDS-PAGE as described. Swanson, et al., *Mol. Cell. Biol.*, 1988, 3, 2237–2241; and Siomi, et al., *Cell*, 1993, 74, 291–298. FXR1 showed a similar RNA-binding profile to FMR1, binding in a moderately (250 mM NaCl) salt-resistant manner to poly(G) and poly(U), but not to poly(A) or poly(C). It is concluded that FXR1, like FMR1, has characteristics of an RNA-binding protein.

The carboxyl portion of *X. laevis* FXR1 (amino acids 500–649) was produced in *E. coli*, purified, and used for immunizations of mice to produce specific antibodies to FXR1. An immunoblot with the serum of an immunized mouse indicated that the serum shows reactivity towards a 70 kD protein, which corresponds to the shorter form of FXR1 in HeLa cells. With longer exposure of same gel, several additional bands near the 70 kD protein were observed. It appears likely that in HeLa cells the shorter form of FXR1 is much more abundant than other forms of FXR1. The serum of the mouse was specific to FXR1; it immunoprecipitated both isoforms of human FXR1 but not FMR1 produced in vitro by transcription/translation of the corresponding cDNAs. Crossreacting proteins of similar size were observed in monkey and chicken cells. A band of lower apparent molecular mass, about 47 kD, and much weaker bands at about 68–70 kD are detected in *D. melanogaster* cells.

The cellular localization of the FXR1 protein was studied by immunofluorescence microscopy in HeLa cells using the antibodies to FXR1 and showed cytoplasmic localization with no significant staining in the nucleus. It has been previously shown that human FMR1 has cytoplasmic localization (Devys, et al., *Nature Genet.*, 1993, 4, 335–340) and the antibodies for human FMR1 which had been raised in our laboratory (Siomi, et al., *Cell*, 1993, 74, 291–298) also showed a cytoplasmic localization of FMR1 in HeLa cells.

Mapping of FXR1 was carried out to determine the chromosomal location of FXR1. Reaction conditions allowed specific amplification of the human gene in a background of either rodent or yeast DNA. In the mapping panel, the cell line containing chromosome 12 contained an amplified fragment of the correct size, 161 bp, whereas none of the other samples contained the amplified fragment of interest. Therefore, FXR1 was tentatively assigned to human chromosome 12. The faint signal in the chromosome 21 lane likely results from some contamination of this hybrid with chromosome 12 material.

The same set of primers was used to screen pools from the Washington University CGM YAC library (Green, et al., *Proc. Natl. Acad. Sci. USA*, 1990, 87, 1213–1217) using the same conditions described for the mapping panel. Two YAC clones containing FXR1 were identified: 1) A192D7; and 2) B105H7. Fluorescence in situ hybridization (Janne, et al., *Cylogenet. Cell Genet.*, 1994, 66, 164–166) using both of these two YACs localized FXR1 to chromosome 12q13, thus confirming the somatic hybrid data.

To determine the expression of FXR1 mRNA in different tissues reverse transcription-polymerase chain reaction (RT-PCR) were performed. Specific non-crossreacting primers were designed to amplify FXR1 and FMR1. FXRI mRNAs were detected in all tissues tested, but different size bands were observed in various tissues. For example, while HeLa cells contain only one FXRI mRNA, at least two forms are detected in brain and testis, and in heart there is an additional larger form. The major smaller HeLa band was cloned and sequenced and its sequence corresponded to the shorter cDNA FXR1 form described above. These findings suggest that there is considerable tissue-specific alternative splicing of FXRI pre-mRNA at least for the carboxyl part and immediate 3' UTR of the mRNA. A similar complex pattern of expression has been reported for FMR1 (Verkerk, et al., Hum. Mol. Genet., 1993, 2, 399–404), although multiple forms of FMR1 were observed by RT-PCR under the conditions used in the experiment.

Most patients with fragile X mental retardation syndrome do not express FMR1 mRNA or protein (Pieretti, et al., Cell, 1991, 66, 817–822; Verheij, et al., Nature, 1993, 363, 722–724; and Siomi, et al., Cell, 1993, 74, 291–298). It was, therefore, of particular interest to determine if the expression of the related protein, FXR1, is also affected in these patients. RT-PCR and immunoblotting were carried out on lymphoblastoid cells of a fragile X patient and his normal sibling (Siomi, et al., Cell, 1993, 74, 291–298). By RT-PCR, both the normal sibling and the patient express FXR1 mRNA, while the patient, as expected, does not express FMR1 mRNA. The same is seen for the protein products of FXR1 and FMR1, respectively. Because of inherent limitations of RT-PCR it is not possible to draw quantitative conclusions from this experiment. It does, however, appear from the immunoblotting experiments that the amount of FXR1 produced in the patient cells is not reduced compared to normal. Thus, FXR1 expression is not drastically effected by the lack of expression of FMR1, and therefore, the FXR1 gene expression in lymphoblastoid cells does not appear to be linked to that of the FMR1 gene.

FXR1 has high amino acid sequence identity to FMR1 in the region containing the KH domains and is very similar to FMR1 within the amino terminal domain. The carboxyl portion of FXR1 is, however, quite different from that of FMR1. Using RT-PCR and primers specific to the carboxyl terminus of FXR1, different size bands were detected in tissues tested. In fact, two alternatively spliced forms of the human FXR1 mRNAs encoding different isoforms have been isolated. It has been shown that alternative splicing, which occurs in both human and mouse FMR1, results in the production of several isoforms that differ at the carboxyl ends but not in the amino terminus of FMR1 (Ashley, et al., Nature Genet., 1993, 4, 244–251; and Verkerk, et al., Hum. Mol. Genet., 1993, 2, 399–404). Taken together, considerable diversity is observed at the carboxyl terminus of both FMR1 and FXR1 proteins. Many genes are subject to alternative splicing which can introduce functional diversity to the products of a single gene. In most cases, this gives rise to protein isoforms sharing extensive legions of identity and varying only in specific domains, thereby allowing for the fine regulation of protein function. The findings of FMR1 and FXR1 isoforms mentioned above suggest that the carboxyl terminus may be involved in the determination of the localization, or regulatory or catalytic specificities in the different members of the FMR1 family. It should be noted that taking into account the relative abundance of different transcripts in various tissues, there may be tissue-specific functions for the various isoforms of FXR1, which may be in contrast to FMR1. Ashley, et al., Nature Genet., 1993, 4, 244–251; and Verkerk, et al., Hum. Mol. Genet., 1993, 2, 399–404.

Both FMR1 and FXR1 have been well conserved through evolution, probably reflecting their essential roles in cells, although the functions of FXR1 and FMR1 have not yet been elucidated. FMR1 and FXR1 have strong structural similarity, are both cytoplasmic and have similar RNA-binding activities in vitro. It, therefore, appears that the biological function of FXR1 protein may be strongly related to that of FMR1. However, if redundancy of FMR1 and FXR1 functions exists, it must only be partial. This follows from the fact that an apparently normal FXR1 mRNA and protein are expressed in lymphoblastoid cells of a patient with fragile X syndrome, while FMR1 mRNA and protein are not expressed in these cells (Pieretti, et al., Cell, 1991, 66, 817–822; Verheij, et al., Nature, 1993, 363, 722–724; and Siomi, et al., Cell, 1993, 74, 291–298). It has been suggested that FMR1 has an important physiological function in neurological tissues as the intragenic mutation in FMR1 (Ile-304→Asn substitution) is directly responsible for the clinical abnormalities, particularly mental retardation, of the fragile X syndrome (De Boulle, et al., Nature Genet., 1993, 3, 31–35).

To produce FXR1 gene knockout mice, several mouse FXR1 genomic clones have been isolated. The intron-exon boundaries around exon 2 and 3 of mouse FXR1 are identical to those of human FMR1, which has been determined to comprise of 17 exons spanning 38 kb at Xq27.3. Eichler, et al., Hum. Mol. Genet., 1993, 2, 1147–1153. The segment containing amino acid 331–396 of FMR1 which is absent from FXR1 and from the X. laevis FMR1 cDNA exactly corresponds to exons 11 and 12 of FMR1.

Example 2A

Materials and Methods

The in vitro transcription-translation reaction was performed using the TNT coupled reticulocyte lysate system (Promega Biotech) in the presence of ($^{35}$S) methionine (Amersham). Truncated FMR1 peptides were produced from pHHSI-F27X (Siomi, et al., Cell, 1993, 74, 291–298) digested at either KpnI (nucleotide 1324 (Verkerk, et al., Cell, 1991, 65, 905–914)) (FMR1-KpnI) or NdeI at nucleotide 740 (FMR1-NdeI). The full length FMR1 was produced from the same plasmid DNA but undigested. FXR2 is from the pET28a-FXR2s plasmid. An EcoRI fragment of pGAD-FXR2s isolated from the two hybrid system was cloned into the pET28a vector to generate pET28a-FXR2S. In vitro-produced proteins were analyzed by SDS-PAGE followed by fluorography. pGST-FXR2 was constructed by inserting an EcoRI fragment of FXR2s into pGST-1λT (Pharmacia). The bacterially expressed fusion protein (GST-FXR2) and GST was purified as described by the manufacturer. 2 µg of purified GST or GST-FXR2 was incubated with 10 µl of the in vitro translated proteins and 25 µL of glutathione-Sepharose (Pharmacia) in 500 µl of binding buffer (50 mM Tris-HCl pH 7.5, 500 mM NaCl, 2 mM EDTA, 0.1% NP40, 5 µg/ml leupeptin and 0.5% aprotinin). Following incubation for 60 minutes at 4° C., the resin was sedimented, washed with binding buffer, and the bound fraction was eluted and analyzed by SDS-PAGE followed by fluorography.

Monoclonal antibodies were raised in mouse against a His6-FXR2s fusion protein from the pET28a-FXR2s plasmid. The fusion protein was expressed in the E. coli strain BL21(DE3)pLysS and purified by metal chelation chromatography as described by the manufacturer (Novogen). Immunofluorescence microscopy on HeLa cells was carried out as previously described (Choi, et al., J. Cell Biol., 1984, 99, 197–204) using hybridoma culture supernatant of monoclonal antibody A66 which was used without dilution. Immunoprecipitations were carried out in the presence of the nondenaturing zwitterionic detergent Empigen BB. Choi, et al., *J. Cell Biol.,* 1984, 99, 197–204. The immunoprecipitates were analyzed by SDS-polyacrylamide gel electrophoresis followed by fluorography. One μl of mouse ascites fluid was used for immunoprecipitation. Immunoblotting was carried out as described using undiluted hybridoma culture supernatant of monoclonal antibody A66. Full length FXR2 produced in vitro was from one of the library isolates cloned into the pGEM7Z vector. The FXR1 peptide was produced. The anti FMR1 monoclonal antibody EF8 was used as control.

Somatic Cell Hybrid Panel #2 was purchased from the Coriell Institute Cell Repository. This panel consists of DNA isolated from 24 human/rodent somatic cell hybrids each retaining a single intact human chromosome. Primers were designed to generate a PCR product of 175 hp from a portion of the 3' untranslated end of the FXR2 gene. The primer (Genosys, inc.) sequences are: forward: 5'-CAGGGTCATACCCCCTCC-3' (SEQ ID NO:9) and reverse: 5'-CTGAACGGTCAAATCTGGGT-3' (SEQ ID NO:10).

PCR reactions were performed in a Perkin-Elmer 480 thermal cycler. Reaction volume of the PCR amplifications was 50 μl containing 50 ng of genomic DNA, 200 mM dNTP, and 2.5 units AmpliTaq DNA polymerase in Perkin-Elmer Buffer 1. Samples were overlaid with light mineral oil and processed through one step of denaturation (95° C. for 6 minutes), 26 cycles of denaturation (95° C. for 1 minute), annealing (55° C. for 2 minutes), and elongation (72° C. for 2 minutes), followed by elongation for one cycle (7 minutes at 72° C.). The PCR products were analyzed by electrophoresis in a 3% NuSieve/agarose gel.

For FISH analysis, an arrayed Chromosome 17 cosmid library constructed from flow-sorted chromosome 17 material by L. Deavan (Los Alamos National Laboratory) was screened for cosmids containing FXR2 using the full-length FXR2 cDNA as probe. Three of the cosmids that hybridized to FXR2 were used as templates for PCR with the primers described above and their PCR products, sequenced as per manufacturer's instructions (fmol sequencing kit, Promega). DNA was isolated from two of these cosmids, labeled with digoxigenin, hybridized to DAPI stained metaphase chromosomes and detected with rhodamine for FISH analysis as described. Pinkel, et al., *Proc. Natl. Acad. Sci. USA,* 1986, 83, 2934–2938. Simultaneously, a marker specific for the centromeric region of chromosome 17 was prepared by PCR amplification of alpha satellite DNA (Weier, et al., *Hum. Genet.,* 1991, 87, 489–494) using DNA from a human chromosome 17-only somatic cell hybrid, labeled with biotin and detected with FITC using a triple band pass filter.

The human brain cDNA library, yeast strains and yeast plasmids pGBT9, pGAD424, pVA3, and pTD1 were from Clontech Incorporated. The manipulation of yeast and the library screening were according to the conditions suggested by the manufacturer. Plasmids pVA3 and pTD1 contain a murine p53/GAL4 DNA binding domain and an SV40 large T-antigen/GALA activation domain hybrid respectively, which served as a positive control for interaction. FMR1 cDNA was from EcoRI-NsiI fragment in pF27X (Siomi, et al., *Cell,* 1993, 74, 291–298), in which the EcoRI site was blunted and the resulting fragment was inserted into pGBTP9 or pGAD424 between SmaI and PstI sites to create pGBT-FMR1 or pGAD-FMR1. As low basal levels of HIS3 expression in the HF7C host strain were observed, 15 mM 3-aminotriazole (3-AT) (Sigma) was added to the selection medium during the screen to suppress growth of transformants containing noninteracting hybrid proteins.

Example 2B

The yeast two-hybrid system was used to identify proteins that interact with FMR1. Fields, et al., *Nature,* 1989, 340, 245–246. FMR1 was fused to the DNA binding domain of the yeast transcription factor GALA (GALA$_{1-147}$-FMR1) as a bait. As a target a human brain cDNA library which was fused to the GALA activation domain was used. The selection in yeast strain HF7C carrying both HIS3 and LacZ reporters under the control of GAL4-responsive elements was performed. Approximately 1×10$^7$ yeast transformants were screened. Eleven colonies showed both histidine prototrophy and β-galactosidase activity. From these 11 colonies, we recovered fusion plasmids that conferred Hie and blue color to reporter strains only in the presence of GALA$_{1-147}$-FMR1. Sequencing of the 11 clones revealed that they were all derived from the same cDNA. As the sequences showed significant homology with that of FMR1 and to another recently described FMR1 homologue, FXR1, the protein was named FXR2 (Fragile X related). The FXR2 clone which turned out to be a partial cDNA, (~1.2 kb) designated FXR2s (amino acids 14–426, see below), was retransformed into a host strain and the specificity of the interaction between FXR2s and FMR1 was further tested (Table 1). Visual inspection of activation of the HIS3 and LacZ reporters showed that FMR1 interacted specifically with FXR2s. Reciprocal exchange of GAL4 peptides, to which FMR1 and FXR2s were fused, did not affect the interaction. FXR2s was also capable of associating with itself, whereas no FMR1-FMR1 interaction was detected in the assay. The interactions observed in the two-hybrid system of FXR2s with FMR1 and with itself were subsequently confirmed for the full-length FXR2 proteins.

To isolate full length clones, the partial FXR2 cDNA (FXR2s) described above was used as a probe to screen a human fetal brain cDNA. The three largest overlapping clones contained an open reading frame of 673 amino acids with a predicted molecular mass of 74 kDa. Northern blot hybridization using labeled FXR2s cDNA as probe detected a transcript of approximately 3.0 kb in HeLa cells and in mouse brain, indicating that the 2.9 kb of cDNA whose sequence is shown contains full-length or near full-length mRNA of this protein. The sequence context of the putative first AUG conforms to the Kozak consensus sequence for preferred translation start sites. Kozak, *J. Cell Biol.,* 1989, 108, 229. Unlike FMR1 mRNA, the 5' UTR of FXR2 does not contain CGG repeats, nor are there any other striking characteristics in the 5'- or 3'-untranslated regions. Homology searches with the predicted protein sequence identified significant similarity with the FMR1 protein (~60% identity) and with a recently described homologue, FXR1. In particular, like FMR1 and FXR1, FXR2 also contains two highly conserved KH domains, the sequence motifs characteristic of RNA binding proteins of this family. Siomi, et al., *Nucl. Acids Res.,* 1993, 21, 1193–1198; and Burd, et al., *Science,* 1994, 265, 615–621. In this region, the similarity between the three proteins is as high as 90%. Additionally, the spacing between the two KH domains is identical in all three proteins. In the carboxyl terminal portion, the similarity between FXR2 and FMR1 decreases gradually. Nevertheless, the strong overall similarity indicates that these proteins belong to the same family. The region carboxyl terminal to the KH domains in FXR2 is very basic and is rich in serines, arginines, glycines and prolines. The last few amino acids of all three proteins contain the same sequence NGVS/P (SEQ ID NO:13).

To further confirm and characterize the FMR1-FXR2 interaction, in vitro binding assays were performed. The FXR2s peptide was expressed as a fusion protein with bacterial glutathione S-transferase (GST). The FMR1 protein was produced and labeled with ($^{35}$S)methionine by in vitro transcription-translation in reticulocyte lysate. The purified GST protein or GST-FXR2 fusion protein immobilized on glutathione-Sepharose was incubated with either labeled FMR1 or, as a control, the hnRNP K protein (Siomi, et al., *Nucl. Acids Res.,* 1993, 21, 1193–1198; and Burd, et al., *Science,* 1994, 265, 615–621) which also contains KH domains. Following washing, bound GST fusion protein and any associated proteins were dissociated by boiling in SDS-containing buffer and analyzed by SDS-polyacrylamide gel electrophoresis (PAGE). Full-length FMR1 bound specifically to the immobilized GST-FXR2, but not to GST alone. As the FXR2 sequence bears strong similarity to the amino-terminus of FMR1, we tested whether the protein-interaction domain of FMR1 was also located in this region. We produced peptides from truncated transcripts generated by digestions of the FMR1 cDNA with KpnI or NdeI. The peptides from KpnI-truncated transcripts were still capable of interacting with FXR2, indicating that, like FXR2, the carboxyl terminus of FMR1 is not necessary for the oligomerization. The region between NdeI and KpnI is required for the interaction with FXR2, since the peptides from NdeI-truncated transcripts, in which the KH domains were deleted, showed little or no binding. The in vitro translated FXR2 also bound to the GST-FXR2, confirming the observation in the two-hybrid system that FXR2 was able to homo-oligomerize. A weak interaction was also detected with a fragment of hnRNP K, the reason for which are presently not understood. The interaction appears to be of high affinity as the washing conditions were stringent, containing 500 mM NaCl in the buffer. In addition, the interaction could also be observed by a far-Western blot assay, in which the ($^{35}$S) methionine-FMR1 specifically bound to FXR2 produced and purified in *E. coli* and immobilized on a nitrocellulose membrane. FXR2 is capable of interacting with FMR1 and with itself in vitro, with high affinity and specificity.

Monoclonal antibodies against FXR2 were produced in mice. Immunoprecipitations with one of the monoclonal antibodies that we have characterized, A42, of FMR1 and FXR2 proteins produced in vitro by transcription/translation demonstrated that it reacted specifically with FXR2 that migrates as a ~95 kD band, and did not crossreact with FMR1. By immunoblotting, A66 (a monoclonal antibody to FXR2 with similar specificity to A42) detected a single band of ~95 kD in total HeLa cell material. The intracellular localization of FXR2 was investigated in HeLa cells by immunofluorescence microscopy. Immunostaining with the monoclonal antibody A66 showed that FXR2, like FMR1 (Devys, et al., *Nature Genet.,* 1993, 4, 335–340), is also present in the cytoplasm. HeLa cells which express FXR2 protein tagged with the Myc-epitope at its amino-terminus detected using a monoclonal antibody directed against Mycepitope also showed cytoplasmic staining. The localization of both proteins to the cytoplasm and their expression in the same cell type (e.g., HeLa) suggests that the FMR1-FXR2 interaction is likely to be biologically relevant.

The chromosomal localization of the FXR2 gene in humans was determined. Primers derived from the 3'-untranslated region of FXR2 allowed specific amplification of the human gene in a background of rodent DNA. PCR amplification of the hybrid cell line with chromosome 17 generated an amplified fragment of the correct size, 175 bp, as predicted from the cDNA sequence, whereas none of the other cell lines showed the amplified fragment of interest. Therefore, FXR2 was tentatively assigned to human chromosome 17. For fluorescent in situ hybridization (FISH) analysis, an arrayed chromosome 17 specific cosmid library was screened by hybridization using full length FXR2 cDNA as probe. Each of three cosmids, located in the array at positions, 58G2, 98F2 and 148C9, was confirmed by PCR to contain the correctly sized 175 hp fragment using the same 3'-untranslated primers used in the somatic cell hybrid panel analysis. The sequence of these PCR products from the cosmids matched the sequence of FXR2 perfectly. The position of FXR2 at 17p13.1 is indicated by the red signal and that of the chromosome 17 centromeric marker by the green signal. Further FISH analysis with the FXR2 cosmids and a probe specific for the Miller-Dieker Syndrome region (17p13.3), a brain malformation manifested by a smooth cerebral surface and abnormal neuronal migration, demonstrated that FXR2 maps proximal to this locus.

Using anti-FXR2 antibodies, FXR2 was detected in the cytoplasm. This is a similar staining pattern to that observed with antibodies to FMR1. Verheij, et al., *Nature,* 1993, 363, 722–724; and Devys, et al., *Nature Genet.,* 1993, 4, 335–340. Significantly, FXR2 shares strong similarity with FMR1, a further indication that the FMR1-FXR2 association is biologically meaningful.

TABLE 1

Interaction of FXR2 with related proteins

| PGBT- | pGAD- | His | β-galactosidase |
|---|---|---|---|
| pVA3 | pTD1 | + | blue |
| pGBT9 | pGAD424 | – | white |
| -FMR1 | pGAD424 | – | white |
| -FMR1 | -FXR2s | + | blue |
| -FXR2s | -FXR2s | + | blue |
| -FXR2s | -FMR1 | + | blue |
| -FMR1 | -FMR1 | – | white |
| pGBT9 | -FXR2s | – | white |
| -FXR2s | pGAD424 | – | white |
| pVA3 | -FXR2s | – | white |
| -FXR2s | PTD1 | – | white |

Table 1: Interaction of FMR1 and FXR2 in the yeast two-hybrid system. Individual colonies of HF7C yeast cells that contained pairs of the indicated plasmids were streaked with toothpicks onto duplicate Trp-Leu- plates, and two days later replica plated onto either a Trp-Leu-His- plate containing 15 mM 3-aminotriazole (Sigma) or a filter paper (Grade 413, VWR Scientific) that was then incubated for a β-galactosidase filter assay. Interaction results in activation of the HIS3 and the LacZ reporters, growing in the absence of histidine or turning blue by galactosidase filter assay are indicated.

We claim:

1. An isolated antibody which binds to an epitope on SEQ ID NO:4, wherein said antibody does not bind to FMR1.

2. The antibody of claim 1 which binds to an epitope within amino acids 380 to 621 of SEQ ID NO:4.

3. The antibody of claim 1 which binds to an epitope within amino acids 535 to 621 of SEQ ID NO:4.

4. The antibody of claim 1 wherein said antibody is a monoclonal antibody.

5. An isolated antibody which binds to an epitope on SEQ ID NO:6, wherein said antibody does not bind to FMR1.

6. The antibody of claim 5 which binds to an epitope within amino acids 390 to 673 of SEQ ID NO:6.

7. The antibody of claim 5 which binds to an epitope within amino acids 574 to 673 of SEQ ID NO:6.

8. The antibody of claim 5 wherein said antibody is a monoclonal antibody.

9. An improved method of screening individuals for Fragile X disease comprising the steps of:

contacting a sample of tissue or body fluid from said individual with antibodies that bind to FMR1 but that do not bind to FXR1 or FXR2; and determining the presence or absence of binding of said antibodies to FMR1 in said sample;

wherein an absence or deficiency of binding of said antibodies is indicative of an individual having Fragile X disease.

* * * * *

UNITED STATES PATENT AND TRADEMARK OFFICE
CERTIFICATE OF CORRECTION

PATENT NO. : 5,876,949
DATED : March 2, 1999
INVENTOR(S) : Dreyfuss et al.

It is certified that error appears in the above-identified patent and that said Letters Patent is hereby corrected as shown below:

Column 1, line 3,

--GOVERNMENT SUPPORT

This invention was supported by funds from the U.S. Government (NIH Grant No. 5 RO1 GM37125) and the U.S. Government may therefor have certain rights in the invention.--

Col. 1, line 16, please delete "*Gemone*" and insert therefor --*Genome*--;
Col. 5, line 10, please delete the word "are";
Col. 12, line 6, please delete "there" and insert therefor --their--;
Col. 19, line 57, please delete "a" and insert therefor --are--.

Signed and Sealed this

Fourth Day of January, 2000

Attest:

Attesting Officer

*Acting Commissioner of Patents and Trademarks*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
  ( A ) LENGTH: 4362 base pairs
  ( B ) TYPE: nucleic acid
  ( C ) STRANDEDNESS: double
  ( D ) TOPOLOGY: linear ( i i ) MOLECULE TYPE: cDNA ( i x ) FEATURE:
  ( A ) NAME/KEY: CDS
  ( B ) LOCATION: 220..2118

( x i ) SEQUENCE DESCRIPTION: SEQ ID NO:1:

```
ACGGCGAGCG   CGGGCGGCGG   CGGTGACGGA   GGCGCCGCTG   CCAGGGGCG    TGCGGCAGCG        60
CGGCGGCGGC   GGCGGCGGCG   GCGGCGGCGG   AGGCGGCGGC   GGCGGCGGCG   GCGGCGGCGG       120
AGGCGGCGGC   GGCGGCGGCG   GCGGCGGCGG   CTGGGCCTCG   AGCGCCCGCA   GCCCACCTCT       180
CGGGGGCGGG   CTCCCGGCGC   TAGCAGGGCT   GAAGAGAAGA   TGGAGGAGCT   GGTGGTGGAA       240
GTGCGGGGCT   CCAATGGCGC   TTTCTACAAG   GCATTTGTAA   AGGATGTTCA   TGAAGATTCA       300
ATAACAGTTG   CATTTGAAAA   CAACTGGCAG   CCTGATAGGC   AGATTCCATT   TCATGATGTC       360
AGATTCCCAC   CTCCTGTAGG   TTATAATAAA   GATATAAATG   AAAGTGATGA   AGTTGAGGTG       420
TATTCCAGAG   CAAATGAAAA   AGAGCCTTGC   TGTTGGTGGT   TAGCTAAAGT   GAGGATGATA       480
AAGGGTGAGT   TTTATGTGAT   AGAATATGCA   GCATGTGATG   CAACTTACAA   TGAAATTGTC       540
ACAATTGAAC   GTCTAAGATC   TGTTAATCCC   AACAAACCTG   CCACAAAAGA   TACTTTCCAT       600
AAGATCAAGC   TGGATGTGCC   AGAAGACTTA   CGGCAAATGT   GTGCCAAAGA   GGCGGCACAT       660
AAGGATTTTA   AAAAGGCAGT   TGGTGCCTTT   TCTGTAACTT   ATGATCCAGA   AAATTATCAG       720
CTTGTCATTT   TGTCCATCAA   TGAAGTCACC   TCAAAGCGAG   CACATATGCT   GATTGACATG       780
CACTTTCGGA   GTCTGCGCAC   TAAGTTGTCT   CTGATAATGA   GAAATGAAGA   AGCTAGTAAG       840
CAGCTGGAGA   GTTCAAGGCA   GCTTGCCTCG   AGATTTCATG   AACAGTTTAT   CGTAAGAGAA       900
GATCTGATGG   GTCTAGCTAT   TGGTACTCAT   GGTGCTAATA   TTCAGCAAGC   TAGAAAAGTA       960
CCTGGGGTCA   CTGCTATTGA   TCTAGATGAA   GATACCTGCA   CATTTCATAT   TTATGGAGAG      1020
GATCAGGATG   CAGTGAAAAA   AGCTAGAAGC   TTTCTCGAAT   TGCTGAAGA   TGTAATACAA      1080
GTTCCAAGGA   ACTTAGTAGG   CAAAGTAATA   GGAAAAAATG   GAAAGCTGAT   TCAGGAGATT      1140
GTGGACAAGT   CAGGAGTTGT   GAGGGTGAGG   ATTGAGGCTG   AAAATGAGAA   AAATGTTCCA      1200
CAAGAAGAGG   AAATTATGCC   ACCAAATTCC   CTTCCTTCCA   ATAATTCAAG   GGTTGGACCT      1260
AATGCCCCAG   AAGAAAAAAA   ACATTTAGAT   ATAAAGGAAA   ACAGCACCCA   TTTTCTCAA      1320
CCTAACAGTA   CAAAAGTCCA   GAGGGTGTTA   GTGGCTTCAT   CAGTTGTAGC   AGGGGAATCC      1380
CAGAAACCTG   AACTCAAGGC   TTGGCAGGGT   ATGGTACCAT   TTGTTTTTGT   GGGAACAAAG      1440
GACAGCATCG   CTAATGCCAC   TGTTCTTTTG   GATTATCACC   TGAACTATTT   AAAGGAAGTA      1500
GACCAGTTGC   GTTTGGAGAG   ATTACAAATT   GATGAGCAGT   TGCGACAGAT   GGAGCTAGT       1560
TCTAGACCAC   CACCAAATCG   TACAGATAAG   GAAAAAAGCT   ATGTGACTGA   TGATGGTCAA      1620
GGAATGGGTC   GAGGTAGTAG   ACCTTACAGA   AATAGGGGC   ACGGCAGACG   CGGTCCTGGA      1680
```

```
TATACTTCAG  GAACTAATTC  TGAAGCATCA  AATGCTTCTG  AAACAGAATC  TGACCACAGA   1740

GACGAACTCA  GTGATTGGTC  ATTAGCTCCA  ACAGAGGAAG  AGAGGGAGAG  CTTCCTGCGC   1800

AGAGGAGACG  GACGGCGGCG  TGGAGGGGGA  GGAAGAGGAC  AAGGAGGAAG  AGGACGTGGA   1860

GGAGGCTTCA  AAGGAAACGA  CGATCACTCC  CGAACAGATA  ATCGTCCACG  TAATCCAAGA   1920

GAGGCTAAAG  GAAGAACAAC  AGATGGATCC  CTTCAGATCA  GAGTTGACTG  CAATAATGAA   1980

AGGAGTGTCC  ACACTAAAAC  ATTACAGAAT  ACCTCCAGTG  AAGGTAGTCG  GCTGCGCACG   2040

GGTAAAGATC  GTAACCAGAA  GAAAGAGAAG  CCAGACAGCG  TGGATGGTCA  GCAACCACTC   2100

GTGAATGGAG  TACCCTAAAC  TGCATAATTC  TGAAGTTATA  TTTCCTATAC  CATTTCCGTA   2160

ATTCTTATTC  CATATTAGAA  AACTTGTTA   GGCCAAAGAC  AAATAGTAGG  CAAGATGGCA   2220

CAGGGCATGA  AATGAACACA  AATTATGCTA  AGAATTTTTT  ATTTTTGGT   ATTGGCCATA   2280

AGCAACAATT  TTCAGATTTG  CACAAAAAGA  TACCTTAAAA  TTTGAAACAT  TGCTTTTAAA   2340

ACTACTTAGC  ACTTCAGGGC  AGATTTTAGT  TTTATTTCT   AAAGTACTGA  GCAGTGATAT   2400

TCTTTGTTAA  TTTGGACCAT  TTTCCTGCAT  TGGGTGATCA  TTCACCAGTA  CATTCTCAGT   2460

TTTTCTTAAT  ATATAGCATT  TATGGTAATC  ATATTAGACT  TCTGTTTTCA  ATCTCGTATA   2520

GAAGTCTTCA  TGAAATGCTA  TGTCATTTCA  TGTCCTGTGT  CAGTTTATGT  TTTGGTCCAC   2580

TTTTCCAGTA  TTTTAGTGGA  CCCTGAAATG  TGTGTGATGT  GACATTGTC   ATTTTCATTA   2640

GCAAAAAAG   TTGTATGATC  TGTGCCTTTT  TTATATCTTG  GCAGGTAGGA  ATATTATATT   2700

TGGATGCAGA  GTTCAGGGAA  GATAAGTTGG  AAACACTAAA  TGTTAAAGAT  GTAGCAAACC   2760

CTGTCAAACA  TTAGTACTTT  ATAGAAGAAT  GCATGCTTTC  CATATTTTTT  TCCTTACATA   2820

AACATCAGGT  TAGGCAGTAT  AAAGAATAGG  ACTTGTTTTT  GTTTTGTTT   TGTTGCACTG   2880

AAGTTTGATA  AATAGTGTTA  TTGAGAGAGA  TGTGTAATTT  TTCTGTATAG  ACAGGAGAAG   2940

AAAGAACTAT  CTTCATCTGA  GAGAGGCTAA  AATGTTTTCA  GCTAGGAACA  AATCTTCCTG   3000

GTCGAAAGTT  AGTAGGATAT  GCCTGCTCTT  TGGCCTGATG  ACCAATTTTA  ACTTAGAGCT   3060

TTTTTTTTA   ATTTGTCTG   CCCCAAGTTT  TGTGAAATTT  TTCATATTTT  AATTTCAAGC   3120

TTATTTGGA   GAGATAGGAA  GGTCATTTCC  ATGTATGCAT  AATAATCCTG  CAAAGTACAG   3180

GTACTTTGTC  TAAGAAACAT  TGGAAGCAGG  TTAAATGTTT  TGTAAACTTT  GAAATATATG   3240

GTCTAATGTT  TAAGCAGAAT  TGGAAAAGAC  TAAGATCGGT  TAACAAATAA  CAACTTTTTT   3300

TTCTTTTTTT  CTTTTGTTTT  TTGAAGTGTT  GGGGTTTGGT  TTTGTTTTTT  GAGTCTTTTT   3360

TTTTTAAGTG  AAATTTATTG  AGGAAAAATA  TGTGAAGGAC  CTTCACTCTA  AGATGTTATA   3420

TTTTTCTTAA  AAAGTAACTC  CTAGTAGGGG  TACCACTGAA  TCTGTACAGA  GCCGTAAAAA   3480

CTGAAGTTCT  GCCTCTGATG  TATTTTGTGA  GTTTGTTTCT  TTGAATTTTC  ATTTTACAGT   3540

TACTTTTCCT  TGCATACAAA  CAAGCATATA  AAATGGCAAC  AAACTGCACA  TGATTTCACA   3600

AATATTAAAA  AGTCTTTTAA  AAAGTATTGC  CAAACATTAA  TGTTGATTTC  TAGTTATTTA   3660

TTCTGGGAAT  GTATAGTATT  TGAAAACAGA  AATTGGTACC  TTGCACACAT  CATCTGTAAG   3720

CTGTTTGGTT  TTAAAATACT  GTAGATAATT  AACCAAGGTA  GAATGACCTT  GTAATGTAAC   3780

TGCTCTTGGG  CAATATTCTC  TGTACATATT  AGCGACAACA  GATTGGATTT  TATGTTGACA   3840

TTTGTTTGGT  TATAGTGCAA  TATATTTTGT  ATGCAAGCAG  TTTCAATAAA  GTTTGATCTT   3900

CCTCTGCTAA  ATTGATGTTG  ATGCAATCCT  TACAAATGAT  TGCTTTTAAA  ATTTTAAGCT   3960

AGGAAAAGAA  ATCTATAGAA  AGTGTTCTGT  TACAAAATGT  AACTGTTACC  ATTGGAAATT   4020

TCACGTCATA  GGAAGTTAGC  CTTTATCTAC  CCAACTTTCA  AGAAGGTTCT  TTAATAAAGC   4080
```

| | | | | | | | |
|---|---|---|---|---|---|---|---|
| GAAAACTCAA | CCAAATGGTA | CTTTTCCACA | GTGTACCATT | AAAATATGCA | CTAGTCTCTT | | 4140 |
| TTTACAAGGC | TGTATTCAGC | AAGGGCCTAA | CTTGCTTAAA | GTGTAATTAC | TAACTTCTAA | | 4200 |
| AACTGTACTT | TGATTCACAT | GTTTTCAAAT | GGAGTTGGAG | TTCATTCATA | TTACAATATT | | 4260 |
| TGTGTGCTAA | ACGTGTATGT | TTTTCAGTTC | AAAGTCATGA | TGTTTTTAAA | ATCTTATTAA | | 4320 |
| AGTTTCAAAA | ATCTGAAGAT | TGTTTATCTA | GATGTAAATT | TT | | | 4362 |

( 2 ) INFORMATION FOR SEQ ID NO:2:

( i ) SEQUENCE CHARACTERISTICS:
        ( A ) LENGTH: 610 amino acid residues
        ( B ) TYPE: amino acid
        ( C ) STRANDEDNESS:
        ( D ) TOPOLOGY: linear ( x i ) SEQUENCE DESCRIPTION: SEQ ID NO:2:

```
Met Glu Glu Leu Val Val Glu Val Arg Gly Ser Asn Gly Ala Phe Tyr
 1               5                  10                  15

Lys Ala Phe Val Lys Asp Val His Glu Asp Ser Ile Thr Val Ala Phe
                 20                  25                  30

Glu Asn Asn Trp Gln Pro Asp Arg Gln Ile Pro Phe His Asp Val Arg
             35                  40                  45

Phe Pro Pro Pro Val Gly Tyr Asn Lys Asp Ile Asn Glu Ser Asp Glu
         50                  55                  60

Val Glu Val Tyr Ser Arg Ala Asn Glu Lys Glu Pro Cys Cys Trp Trp
 65                  70                  75                  80

Leu Ala Lys Val Arg Met Ile Lys Gly Glu Phe Tyr Val Ile Glu Tyr
                 85                  90                  95

Ala Ala Cys Asp Ala Thr Tyr Asn Glu Ile Val Thr Ile Glu Arg Leu
             100                 105                 110

Arg Ser Val Asn Pro Asn Lys Pro Ala Thr Lys Asp Thr Phe His Lys
         115                 120                 125

Ile Lys Leu Asp Val Pro Glu Asp Leu Arg Gln Met Cys Ala Lys Glu
 130                 135                 140

Ala Ala His Lys Asp Phe Lys Lys Ala Val Gly Ala Phe Ser Val Thr
145                 150                 155                 160

Tyr Asp Pro Glu Asn Tyr Gln Leu Val Ile Leu Ser Ile Asn Glu Val
                 165                 170                 175

Thr Ser Lys Arg Ala His Met Leu Ile Asp Met His Phe Arg Ser Leu
             180                 185                 190

Arg Thr Lys Leu Ser Leu Ile Met Arg Asn Glu Glu Ala Ser Lys Gln
         195                 200                 205

Leu Glu Ser Ser Arg Gln Leu Ala Ser Arg Phe His Glu Gln Phe Ile
 210                 215                 220

Val Arg Glu Asp Leu Met Gly Leu Ala Ile Gly Thr His Gly Ala Asn
225                 230                 235                 240

Ile Gln Gln Ala Arg Lys Val Pro Gly Val Thr Ala Ile Asp Leu Asp
                 245                 250                 255

Glu Asp Thr Cys Thr Phe His Ile Tyr Gly Glu Asp Gln Asp Ala Val
             260                 265                 270

Lys Lys Ala Arg Ser Phe Leu Glu Phe Ala Glu Asp Val Ile Gln Val
         275                 280                 285

Pro Arg Asn Leu Val Gly Lys Val Ile Gly Lys Asn Gly Lys Leu Ile
 290                 295                 300

Gln Glu Ile Val Asp Lys Ser Gly Val Val Arg Val Arg Ile Glu Ala
305                 310                 315                 320
```

| Glu | Asn | Glu | Lys | Asn<br>325 | Val | Pro | Gln | Glu<br>330 | Glu | Ile | Met | Pro | Pro<br>335 | Asn |
|---|---|---|---|---|---|---|---|---|---|---|---|---|---|---|
| Ser | Leu | Pro | Ser<br>340 | Asn | Asn | Ser | Arg<br>345 | Val | Gly | Pro | Asn | Ala<br>350 | Pro | Glu | Glu |
| Lys | Lys | His<br>355 | Leu | Asp | Ile | Lys<br>360 | Glu | Asn | Ser | Thr | His<br>365 | Phe | Ser | Gln | Pro |
| Asn | Ser<br>370 | Thr | Lys | Val | Gln | Arg<br>375 | Gly | Met | Val | Pro | Phe<br>380 | Val | Phe | Val | Gly |
| Thr<br>385 | Lys | Asp | Ser | Ile | Ala<br>390 | Asn | Ala | Thr | Val | Leu<br>395 | Leu | Asp | Tyr | His | Leu<br>400 |
| Asn | Tyr | Leu | Lys | Glu<br>405 | Val | Asp | Gln | Leu | Arg<br>410 | Leu | Glu | Arg | Leu | Gln<br>415 | Ile |
| Asp | Glu | Gln | Leu<br>420 | Arg | Gln | Ile | Gly | Ala<br>425 | Ser | Ser | Arg | Pro<br>430 | Pro | Pro | Asn |
| Arg | Thr | Asp<br>435 | Lys | Glu | Lys | Ser | Tyr<br>440 | Val | Thr | Asp | Asp | Gly<br>445 | Gln | Gly | Met |
| Gly | Arg<br>450 | Gly | Ser | Arg | Pro | Tyr<br>455 | Arg | Asn | Arg | Gly | His<br>460 | Gly | Arg | Arg | Gly |
| Pro<br>465 | Gly | Tyr | Thr | Ser | Gly<br>470 | Thr | Asn | Ser | Glu | Ala<br>475 | Ser | Asn | Ala | Ser | Glu<br>480 |
| Thr | Glu | Ser | Asp | His<br>485 | Arg | Asp | Glu | Leu | Ser<br>490 | Asp | Trp | Ser | Leu | Ala<br>495 | Pro |
| Thr | Glu | Glu | Glu<br>500 | Arg | Glu | Ser | Phe | Leu<br>505 | Arg | Arg | Gly | Asp | Arg<br>510 | Arg | Arg |
| Gly | Gly | Gly | Gly | Arg<br>515 | Gly | Gln | Gly<br>520 | Gly | Arg | Gly | Arg | Gly<br>525 | Gly | Gly | Phe |
| Lys | Gly<br>530 | Asn | Asp | Asp | His | Ser<br>535 | Arg | Thr | Asp | Asn | Arg<br>540 | Pro | Arg | Asn | Pro |
| Arg<br>545 | Glu | Ala | Lys | Gly | Arg<br>550 | Thr | Thr | Asp | Gly | Ser<br>555 | Leu | Gln | Ile | Arg | Val<br>560 |
| Asn | Cys | Asn | Asn | Glu<br>565 | Arg | Ser | Val | His | Thr<br>570 | Lys | Thr | Leu | Gln | Asn<br>575 | Thr |
| Ser | Ser | Glu | Gly<br>580 | Ser | Arg | Leu | Arg | Thr<br>585 | Gly | Lys | Asp | Arg | Asn<br>590 | Gln | Lys |
| Lys | Glu | Lys<br>595 | Pro | Asp | Ser | Val | Asp<br>600 | Gly | Gln | Gln | Pro | Leu<br>605 | Val | Asn | Gly |
| Val | Pro<br>610 | | | | | | | | | | | | | | |

( 2 ) INFORMATION FOR SEQ ID NO:3:

( i ) SEQUENCE CHARACTERISTICS:
        ( A ) LENGTH: 1863 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

| ATG | GCG | GAC | GTG | ACG | GTG | GAG | GTT | CGC | GGC | TCT | AAC | GGG | GCT | TTC | TAC | 48 |
|---|---|---|---|---|---|---|---|---|---|---|---|---|---|---|---|---|
| Met<br>1 | Ala | Asp | Val | Thr<br>5 | Val | Glu | Val | Arg | Gly<br>10 | Ser | Asn | Gly | Ala | Phe<br>15 | Tyr | |
| AAG | GGA | TTT | ATC | AAA | GAT | GTT | CAT | GAA | GAC | TCC | CTT | ACA | GTT | GTT | TTT | 96 |
| Lys | Gly | Phe | Ile<br>20 | Lys | Asp | Val | His | Glu<br>25 | Asp | Ser | Leu | Thr | Val<br>30 | Val | Phe | |
| GAA | AAT | AAT | TGG | CAA | CCA | GAA | CGC | CAG | GTT | CCA | TTT | AAT | GAA | GTT | AGA | 144 |
| Glu | Asn | Asn | Trp<br>35 | Gln | Pro | Glu | Arg<br>40 | Gln | Val | Pro | Phe | Asn<br>45 | Glu | Val | Arg | |

| | | | | | | | | | | | | | | | | |
|---|---|---|---|---|---|---|---|---|---|---|---|---|---|---|---|---|
| TTA | CCA | CCA | CCA | CCT | GAT | ATA | AAA | AAA | GAA | ATT | AGT | GAA | GGA | GAT | GAA | 192 |
| Leu | Pro | Pro | Pro | Pro | Asp | Ile | Lys | Lys | Glu | Ile | Ser | Glu | Gly | Asp | Glu | |
| | 50 | | | | 55 | | | | | 60 | | | | | | |
| GTA | GAG | GTA | TAT | TCA | AGA | GCA | AAT | GAC | CAA | GAG | CCA | TGT | GGG | TGG | TGG | 240 |
| Val | Glu | Val | Tyr | Ser | Arg | Ala | Asn | Asp | Gln | Glu | Pro | Cys | Gly | Trp | Trp | |
| 65 | | | | | 70 | | | | | 75 | | | | | 80 | |
| TTG | GCT | AAA | GTT | CGG | ATG | ATG | AAA | GGA | GAA | TTT | TAT | GTC | ATT | GAA | TAT | 288 |
| Leu | Ala | Lys | Val | Arg | Met | Met | Lys | Gly | Glu | Phe | Tyr | Val | Ile | Glu | Tyr | |
| | | | | | 85 | | | | | 90 | | | | | 95 | |
| GCT | GCT | TGT | GAC | GCT | ACT | TAC | AAT | GAA | ATA | GTC | ACA | TTT | GAA | CGA | CTT | 336 |
| Ala | Ala | Cys | Asp | Ala | Thr | Tyr | Asn | Glu | Ile | Val | Thr | Phe | Glu | Arg | Leu | |
| | | | 100 | | | | | 105 | | | | | 110 | | | |
| CGG | CCT | GTC | AAT | CAA | AAT | AAA | ACT | GTC | AAA | AAA | AAT | ACC | TTC | TTT | AAA | 384 |
| Arg | Pro | Val | Asn | Gln | Asn | Lys | Thr | Val | Lys | Lys | Asn | Thr | Phe | Phe | Lys | |
| | | | 115 | | | | | 120 | | | | | 125 | | | |
| TGC | ACA | GTG | GAT | GTT | CCT | GAG | GAT | TTG | AGA | GAG | GCG | TGT | GCT | AAT | GAA | 432 |
| Cys | Thr | Val | Asp | Val | Pro | Glu | Asp | Leu | Arg | Glu | Ala | Cys | Ala | Asn | Glu | |
| | | | 130 | | | | | 135 | | | | | 140 | | | |
| AAT | GCA | CAT | AAA | GAT | TTT | AAG | AAA | GCA | GTA | GGA | GCA | TGC | AGA | ATT | TTT | 480 |
| Asn | Ala | His | Lys | Asp | Phe | Lys | Lys | Ala | Val | Gly | Ala | Cys | Arg | Ile | Phe | |
| 145 | | | | | 150 | | | | | 155 | | | | | 160 | |
| TAC | CAT | CCA | GAA | ACA | ACA | CAG | CTA | ATG | ATA | CTG | TCT | GCC | AGT | GAA | GCA | 528 |
| Tyr | His | Pro | Glu | Thr | Thr | Gln | Leu | Met | Ile | Leu | Ser | Ala | Ser | Glu | Ala | |
| | | | | 165 | | | | | 170 | | | | | 175 | | |
| ACT | GTG | AAG | AGA | GTA | AAC | ATC | TTA | AGT | GAC | ATG | CAT | TTG | CGA | AGT | ATT | 576 |
| Thr | Val | Lys | Arg | Val | Asn | Ile | Leu | Ser | Asp | Met | His | Leu | Arg | Ser | Ile | |
| | | | 180 | | | | | 185 | | | | | 190 | | | |
| CGT | ACG | AAG | TTG | ATG | CTT | ATG | TCC | AGA | AAT | GAA | GAG | GCC | ACT | AAG | CAT | 624 |
| Arg | Thr | Lys | Leu | Met | Leu | Met | Ser | Arg | Asn | Glu | Glu | Ala | Thr | Lys | His | |
| | | | 195 | | | | | 200 | | | | | 205 | | | |
| TTA | GAA | TGC | ACA | AAA | CAA | CTT | GCA | GCA | GCT | TTT | CAT | GAG | GAA | TTT | GTT | 672 |
| Leu | Glu | Cys | Thr | Lys | Gln | Leu | Ala | Ala | Ala | Phe | His | Glu | Glu | Phe | Val | |
| 210 | | | | | 215 | | | | | 220 | | | | | | |
| GTG | AGA | GAA | GAT | TTA | ATG | GGC | CTG | GCA | ATA | GGA | ACA | CAT | GGT | AGT | AAC | 720 |
| Val | Arg | Glu | Asp | Leu | Met | Gly | Leu | Ala | Ile | Gly | Thr | His | Gly | Ser | Asn | |
| 225 | | | | | 230 | | | | | 235 | | | | | 240 | |
| ATC | CAG | CAA | GCT | AGG | AAG | GTT | CCT | GGA | GTT | ACC | GCC | ATT | GAG | CTA | GAT | 768 |
| Ile | Gln | Gln | Ala | Arg | Lys | Val | Pro | Gly | Val | Thr | Ala | Ile | Glu | Leu | Asp | |
| | | | | 245 | | | | | 250 | | | | | 255 | | |
| GAA | GAT | ACT | GGA | ACA | TTC | AGA | ATC | TAC | GGA | GAG | AGT | GCT | GAT | GCT | GTA | 816 |
| Glu | Asp | Thr | Gly | Thr | Phe | Arg | Ile | Tyr | Gly | Glu | Ser | Ala | Asp | Ala | Val | |
| | | | 260 | | | | | 265 | | | | | 270 | | | |
| AAA | AAG | GCT | AGA | GGT | TTC | TTG | GAA | TTT | GTG | GAG | GAT | TTT | ATT | CAG | GTT | 864 |
| Lys | Lys | Ala | Arg | Gly | Phe | Leu | Glu | Phe | Val | Glu | Asp | Phe | Ile | Gln | Val | |
| | | | 275 | | | | | 280 | | | | | 285 | | | |
| CCT | AGG | AAT | CTC | GTT | GGA | AAA | GTA | ATT | GGA | AAA | AAT | GGC | AAA | GTT | ATT | 912 |
| Pro | Arg | Asn | Leu | Val | Gly | Lys | Val | Ile | Gly | Lys | Asn | Gly | Lys | Val | Ile | |
| | 290 | | | | | 295 | | | | | 300 | | | | | |
| CAA | GAA | ATA | GTG | GAC | AAA | TCT | GGT | GTG | GTT | CGA | GTG | AGA | ATT | GAA | GGG | 960 |
| Gln | Glu | Ile | Val | Asp | Lys | Ser | Gly | Val | Val | Arg | Val | Arg | Ile | Glu | Gly | |
| 305 | | | | | 310 | | | | | 315 | | | | | 320 | |
| GAC | AAT | GAA | AAT | AAA | TTA | CCC | AGA | GAA | GAC | GGT | ATG | GTT | CCA | TTT | GTA | 1008 |
| Asp | Asn | Glu | Asn | Lys | Leu | Pro | Arg | Glu | Asp | Gly | Met | Val | Pro | Phe | Val | |
| | | | | 325 | | | | | 330 | | | | | 335 | | |
| TTT | GTT | GGC | ACT | AAA | GAA | AGC | ATT | GGA | AAT | GTG | CAG | GTT | CTT | CTA | GAG | 1056 |
| Phe | Val | Gly | Thr | Lys | Glu | Ser | Ile | Gly | Asn | Val | Gln | Val | Leu | Leu | Glu | |
| | | | 340 | | | | | 345 | | | | | 350 | | | |
| TAT | CAT | ATT | GCC | TAT | CTA | AAG | GAA | GTA | GAA | CAG | CTA | AGA | ATG | GAA | CGC | 1104 |
| Tyr | His | Ile | Ala | Tyr | Leu | Lys | Glu | Val | Glu | Gln | Leu | Arg | Met | Glu | Arg | |
| | | 355 | | | | | 360 | | | | | 365 | | | | |

| | | | | | | | | | | | | | | | | |
|---|---|---|---|---|---|---|---|---|---|---|---|---|---|---|---|---|
| CTA | CAG | ATT | GAT | GAA | CAG | CTG | CGA | CAG | ATT | GGT | TCT | AGG | TCT | TAT | AGC | 1152 |
| Leu | Gln | Ile | Asp | Glu | Gln | Leu | Arg | Gln | Ile | Gly | Ser | Arg | Ser | Tyr | Ser | |
| | 370 | | | | 375 | | | | | 380 | | | | | | |
| GGA | AGA | GGC | AGA | GGT | CGT | CGG | GGA | CCT | AAT | TAC | ACC | TCC | GGT | TAT | GGT | 1200 |
| Gly | Arg | Gly | Arg | Gly | Arg | Arg | Gly | Pro | Asn | Tyr | Thr | Ser | Gly | Tyr | Gly | |
| 385 | | | | | 390 | | | | | 395 | | | | | 400 | |
| ACA | AAT | TCT | GAG | CTG | TCT | AAC | CCC | TCT | GAA | ACG | GAA | TCT | GAG | CGT | AAA | 1248 |
| Thr | Asn | Ser | Glu | Leu | Ser | Asn | Pro | Ser | Glu | Thr | Glu | Ser | Glu | Arg | Lys | |
| | | | | 405 | | | | | 410 | | | | | 415 | | |
| GAC | GAG | CTG | AGT | GAT | TGG | TCA | TTG | GCA | GGA | GAA | GAT | AAT | CGA | GAC | AGC | 1296 |
| Asp | Glu | Leu | Ser | Asp | Trp | Ser | Leu | Ala | Gly | Glu | Asp | Asn | Arg | Asp | Ser | |
| | | | 420 | | | | | 425 | | | | | 430 | | | |
| CGA | CAT | CAG | CGT | GAC | AGC | AGG | AGA | CGC | CCA | GGA | GGA | AGA | GGC | AGA | AGT | 1344 |
| Arg | His | Gln | Arg | Asp | Ser | Arg | Arg | Arg | Pro | Gly | Gly | Arg | Gly | Arg | Ser | |
| | | 435 | | | | | 440 | | | | | | 445 | | | |
| GTT | TCA | GGG | GGT | CGA | GGT | CGT | GGT | GGA | CCA | CGT | GGT | GGC | AAA | TCC | TCC | 1392 |
| Val | Ser | Gly | Gly | Arg | Gly | Arg | Gly | Gly | Pro | Arg | Gly | Gly | Lys | Ser | Ser | |
| | 450 | | | | | 455 | | | | | | 460 | | | | |
| ATC | AGT | TCT | GTG | CTC | AAA | GAT | CCA | GAC | AGC | AAT | CCA | TAC | AGC | TTA | CTT | 1440 |
| Ile | Ser | Ser | Val | Leu | Lys | Asp | Pro | Asp | Ser | Asn | Pro | Tyr | Ser | Leu | Leu | |
| 465 | | | | | 470 | | | | | 475 | | | | | 480 | |
| GAT | AAT | ACA | GAA | TCA | GAT | CAG | ACT | GCA | GAC | ACT | GAT | GCC | AGC | GAA | TCT | 1488 |
| Asp | Asn | Thr | Glu | Ser | Asp | Gln | Thr | Ala | Asp | Thr | Asp | Ala | Ser | Glu | Ser | |
| | | | | 485 | | | | | 490 | | | | | 495 | | |
| CAT | CAC | AGT | ACT | AAC | CGT | CGT | AGG | CGG | TCT | CGT | AGA | CGA | AGG | ACT | GAT | 1536 |
| His | His | Ser | Thr | Asn | Arg | Arg | Arg | Arg | Ser | Arg | Arg | Arg | Arg | Thr | Asp | |
| | | | 500 | | | | | 505 | | | | | 510 | | | |
| GAA | GAT | GCT | GTT | CTG | ATG | GAT | GGA | ATG | ACT | GAA | TCT | GAT | ACA | GCT | TCA | 1584 |
| Glu | Asp | Ala | Val | Leu | Met | Asp | Gly | Met | Thr | Glu | Ser | Asp | Thr | Ala | Ser | |
| | | 515 | | | | | 520 | | | | | 525 | | | | |
| GTT | AAT | GAA | AAT | GGG | CTA | GTC | ACA | GTT | GCA | GAT | TAT | ATT | TCT | AGA | GCT | 1632 |
| Val | Asn | Glu | Asn | Gly | Leu | Val | Thr | Val | Ala | Asp | Tyr | Ile | Ser | Arg | Ala | |
| | 530 | | | | | 535 | | | | | 540 | | | | | |
| GAG | TCT | CAG | AGC | AGA | CAA | AGA | AAC | CTC | CCA | AGG | GAA | ACT | TTG | GCT | AAA | 1680 |
| Glu | Ser | Gln | Ser | Arg | Gln | Arg | Asn | Leu | Pro | Arg | Glu | Thr | Leu | Ala | Lys | |
| 545 | | | | | 550 | | | | | 555 | | | | | 560 | |
| AAC | AAG | AAA | GAA | ATG | GCA | AAA | GAT | GTG | ATT | GAA | GAG | CAT | GGT | CCT | TCA | 1728 |
| Asn | Lys | Lys | Glu | Met | Ala | Lys | Asp | Val | Ile | Glu | Glu | His | Gly | Pro | Ser | |
| | | | | 565 | | | | | 570 | | | | | 575 | | |
| GAA | AAG | GCA | ATA | AAC | GGC | CCA | ACT | AGT | GCT | TCT | GGC | GAT | GAC | ATT | TCT | 1776 |
| Glu | Lys | Ala | Ile | Asn | Gly | Pro | Thr | Ser | Ala | Ser | Gly | Asp | Asp | Ile | Ser | |
| | | | | 580 | | | | | 585 | | | | | 590 | | |
| AAG | CTA | CAG | CGT | ACT | CCA | GGA | GAA | GAA | AAG | ATT | AAT | ACC | TTA | AAA | GAA | 1824 |
| Lys | Leu | Gln | Arg | Thr | Pro | Gly | Glu | Glu | Lys | Ile | Asn | Thr | Leu | Lys | Glu | |
| | | 595 | | | | | 600 | | | | | 605 | | | | |
| GAA | AAC | ACT | CAA | GAA | GCA | GCA | GTC | CTG | AAT | GGT | GTT | TCA | | | | 1863 |
| Glu | Asn | Thr | Gln | Glu | Ala | Ala | Val | Leu | Asn | Gly | Val | Ser | | | | |
| | | 610 | | | | | 615 | | | | | 620 | | | | |

( 2 ) INFORMATION FOR SEQ ID NO:4:

( i ) SEQUENCE CHARACTERISTICS:
        ( A ) LENGTH: 621 amino acid residues
        ( B ) TYPE: amino acid
        ( C ) STRANDEDNESS:
        ( D ) TOPOLOGY: linear ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ala | Asp | Val | Thr | Val | Glu | Val | Arg | Gly | Ser | Asn | Gly | Ala | Phe | Tyr |
| 1 | | | | 5 | | | | | 10 | | | | | 15 | |
| Lys | Gly | Phe | Ile | Lys | Asp | Val | His | Glu | Asp | Ser | Leu | Thr | Val | Val | Phe |

|   |   |   |   |   | 20 |   |   |   |   | 25 |   |   |   |   | 30 |   |   |
|---|---|---|---|---|---|---|---|---|---|---|---|---|---|---|---|---|---|

Glu Asn Asn Trp Gln Pro Glu Arg Gln Val Pro Phe Asn Glu Val Arg
         35                    40                   45

Leu Pro Pro Pro Asp Ile Lys Lys Glu Ile Ser Glu Gly Asp Glu
    50              55                  60

Val Glu Val Tyr Ser Arg Ala Asn Asp Gln Pro Cys Gly Trp Trp
65               70              75                       80

Leu Ala Lys Val Arg Met Met Lys Gly Phe Tyr Val Ile Glu Tyr
             85              90                       95

Ala Ala Cys Asp Ala Thr Tyr Asn Glu Ile Val Thr Phe Glu Arg Leu
        100              105                110

Arg Pro Val Asn Gln Asn Lys Thr Val Lys Lys Asn Thr Phe Phe Lys
        115              120                125

Cys Thr Val Asp Val Pro Glu Asp Leu Arg Glu Ala Cys Ala Asn Glu
    130                  135                140

Asn Ala His Lys Asp Phe Lys Lys Ala Val Gly Ala Cys Arg Ile Phe
145                  150                155                160

Tyr His Pro Glu Thr Thr Gln Leu Met Ile Leu Ser Ala Ser Glu Ala
             165                170                175

Thr Val Lys Arg Val Asn Ile Leu Ser Asp Met His Leu Arg Ser Ile
            180                185                 190

Arg Thr Lys Leu Met Leu Met Ser Arg Asn Glu Glu Ala Thr Lys His
        195                 200                205

Leu Glu Cys Thr Lys Gln Leu Ala Ala Ala Phe His Glu Glu Phe Val
    210                 215                 220

Val Arg Glu Asp Leu Met Gly Leu Ala Ile Gly Thr His Gly Ser Asn
225                 230                 235                240

Ile Gln Gln Ala Arg Lys Val Pro Gly Val Thr Ala Ile Glu Leu Asp
            245                 250                 255

Glu Asp Thr Gly Thr Phe Arg Ile Tyr Gly Glu Ser Ala Asp Ala Val
            260                 265                 270

Lys Lys Ala Arg Gly Phe Leu Glu Phe Val Glu Asp Phe Ile Gln Val
            275                 280                 285

Pro Arg Asn Leu Val Gly Lys Val Ile Gly Lys Asn Gly Lys Val Ile
    290                 295                 300

Gln Glu Ile Val Asp Lys Ser Gly Val Val Arg Val Arg Ile Glu Gly
305                 310                 315                 320

Asp Asn Glu Asn Lys Leu Pro Arg Glu Asp Gly Met Val Pro Phe Val
            325                 330                 335

Phe Val Gly Thr Lys Glu Ser Ile Gly Asn Val Gln Val Leu Leu Glu
            340                 345                 350

Tyr His Ile Ala Tyr Leu Lys Glu Val Glu Gln Leu Arg Met Glu Arg
        355                 360                 365

Leu Gln Ile Asp Glu Gln Leu Arg Gln Ile Gly Ser Arg Ser Tyr Ser
    370                 375                 380

Gly Arg Gly Arg Gly Arg Arg Gly Pro Asn Tyr Thr Ser Gly Tyr Gly
385                 390                 395                 400

Thr Asn Ser Glu Leu Ser Asn Pro Ser Glu Thr Glu Ser Glu Arg Lys
            405                 410                 415

Asp Glu Leu Ser Asp Trp Ser Leu Ala Gly Glu Asp Asn Arg Asp Ser
            420                 425                 430

Arg His Gln Arg Asp Ser Arg Arg Arg Pro Gly Gly Arg Gly Arg Ser
        435                 440                 445

-continued

| | | | | | | | | | | | | | | |
|---|---|---|---|---|---|---|---|---|---|---|---|---|---|---|
| Val | Ser | Gly | Gly | Arg | Gly | Arg | Gly | Gly | Pro | Arg | Gly | Gly | Lys | Ser | Ser |
| | 450 | | | | | 455 | | | | | 460 | | | | |
| Ile | Ser | Ser | Val | Leu | Lys | Asp | Pro | Asp | Ser | Asn | Pro | Tyr | Ser | Leu | Leu |
| 465 | | | | | 470 | | | | | 475 | | | | | 480 |
| Asp | Asn | Thr | Glu | Ser | Asp | Gln | Thr | Ala | Asp | Thr | Asp | Ala | Ser | Glu | Ser |
| | | | | 485 | | | | | 490 | | | | | 495 | |
| His | His | Ser | Thr | Asn | Arg | Arg | Arg | Ser | Arg | Arg | Arg | Thr | Asp |
| | | | 500 | | | | | 505 | | | | 510 | |
| Glu | Asp | Ala | Val | Leu | Met | Asp | Gly | Met | Thr | Glu | Ser | Asp | Thr | Ala | Ser |
| | | | 515 | | | | 520 | | | | | 525 | | | |
| Val | Asn | Glu | Asn | Gly | Leu | Val | Thr | Val | Ala | Asp | Tyr | Ile | Ser | Arg | Ala |
| | | 530 | | | | 535 | | | | | 540 | | | | |
| Glu | Ser | Gln | Ser | Arg | Gln | Arg | Asn | Leu | Pro | Arg | Glu | Thr | Leu | Ala | Lys |
| 545 | | | | | 550 | | | | | 555 | | | | | 560 |
| Asn | Lys | Lys | Glu | Met | Ala | Lys | Asp | Val | Ile | Glu | Glu | His | Gly | Pro | Ser |
| | | | | 565 | | | | | 570 | | | | | 575 | |
| Glu | Lys | Ala | Ile | Asn | Gly | Pro | Thr | Ser | Ala | Ser | Gly | Asp | Asp | Ile | Ser |
| | | | | 580 | | | | | 585 | | | | | 590 | |
| Lys | Leu | Gln | Arg | Thr | Pro | Gly | Glu | Lys | Ile | Asn | Thr | Leu | Lys | Glu |
| | | 595 | | | | | 600 | | | | | 605 | |
| Glu | Asn | Thr | Gln | Glu | Ala | Ala | Val | Leu | Asn | Gly | Val | Ser |
| | 610 | | | | | 615 | | | | | 620 | |

(2) INFORMATION FOR SEQ ID NO:5:

(i) SEQUENCE CHARACTERISTICS:
    (A) LENGTH: 2019 base pairs
    (B) TYPE: nucleic acid
    (C) STRANDEDNESS: double
    (D) TOPOLOGY: linear (xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | GGC | GGC | CTG | GCC | TCT | GGG | GGG | GAT | GTG | GAG | CCG | GGA | CTG | CCC | GTC | 48 |
| Met | Gly | Gly | Leu | Ala | Ser | Gly | Gly | Asp | Val | Glu | Pro | Gly | Leu | Pro | Val | |
| 1 | | | | 5 | | | | | 10 | | | | | 15 | | |
| GAG | GTG | CGC | GGC | TCC | AAC | GGG | GCC | TTC | TAC | AAG | GGC | TTT | GTG | AAG | GAT | 96 |
| Glu | Val | Arg | Gly | Ser | Asn | Gly | Ala | Phe | Tyr | Lys | Gly | Phe | Val | Lys | Asp | |
| | | | 20 | | | | | 25 | | | | | 30 | | | |
| GTC | CAT | GAA | GAC | TCT | GTC | ACC | ATC | TTC | TTT | GAA | AAC | AAC | TGG | CAG | AGT | 144 |
| Val | His | Glu | Asp | Ser | Val | Thr | Ile | Phe | Phe | Glu | Asn | Asn | Trp | Gln | Ser | |
| | | 35 | | | | | 40 | | | | | 45 | | | | |
| GAG | AGA | CAA | ATT | CCT | TTT | GGG | GAT | GTC | CGG | CTA | CCA | CCT | CCA | GCT | GAC | 192 |
| Glu | Arg | Gln | Ile | Pro | Phe | Gly | Asp | Val | Arg | Leu | Pro | Pro | Pro | Ala | Asp | |
| | | 50 | | | | | 55 | | | | | 60 | | | | |
| TAT | AAT | AAG | GAG | ATC | ACA | GAA | GGG | GAT | GAA | GTG | GAG | GTT | TAT | TCT | CGA | 240 |
| Tyr | Asn | Lys | Glu | Ile | Thr | Glu | Gly | Asp | Glu | Val | Glu | Val | Tyr | Ser | Arg | |
| 65 | | | | | 70 | | | | | 75 | | | | | 80 | |
| GCC | AAT | GAA | CAG | GAA | CCT | TGT | GGC | TGG | TGG | CTG | GCC | CGG | GTG | CGG | ATG | 288 |
| Ala | Asn | Glu | Gln | Glu | Pro | Cys | Gly | Trp | Trp | Thr | Ala | Arg | Val | Arg | Met | |
| | | | | 85 | | | | | 90 | | | | | 95 | | |
| ATG | AAG | GGA | GAT | TTC | TAT | GTC | ATT | GAA | TAT | GCT | GCC | TGT | GAT | GCC | ACC | 336 |
| Met | Lys | Gly | Asp | Phe | Tyr | Val | Ile | Glu | Tyr | Ala | Ala | Cys | Asp | Ala | Thr | |
| | | | | 100 | | | | | 105 | | | | | 110 | | |
| TAC | AAT | GAA | ATT | GTT | ACC | CTG | GAG | CGA | CTT | CGG | CCA | GTT | AAT | CCC | AAT | 384 |
| Tyr | Asn | Glu | Ile | Val | Thr | Leu | Glu | Arg | Leu | Arg | Pro | Val | Asn | Pro | Asn | |
| | | | 115 | | | | | 120 | | | | | 125 | | | |
| CCC | CTT | GCA | ACC | AAA | GGC | AGC | TTC | TTC | AAG | GTT | ACC | ATG | GCT | GTG | CCC | 432 |
| Pro | Leu | Ala | Thr | Lys | Gly | Ser | Phe | Phe | Lys | Val | Thr | Met | Ala | Val | Pro | |
| | | 130 | | | | | 135 | | | | | 140 | | | | |

| | | | | | | | | | | | | | | | | |
|---|---|---|---|---|---|---|---|---|---|---|---|---|---|---|---|---|
| GAG | GAT | CTG | AGA | GAA | GCC | TGC | TCC | AAT | GAA | AAC | GTC | CAT | AAA | GAG | TTC | 480 |
| Glu | Asp | Leu | Arg | Glu | Ala | Cys | Ser | Asn | Glu | Asn | Val | His | Lys | Glu | Phe | |
| 145 | | | | 150 | | | | | 155 | | | | | | 160 | |
| AAG | AAA | GCC | CTG | GGA | GCC | AAC | TGC | ATC | TTT | CTC | AAC | ATC | ACA | AAC | AGT | 528 |
| Lys | Lys | Ala | Thr | Gly | Ala | Asn | Cys | Ile | Phe | Thr | Asn | Ile | Thr | Asn | Ser | |
| | | | | 165 | | | | 170 | | | | | 175 | | | |
| GAG | CTC | TTC | ATT | CTG | TCA | ACC | ACA | GAA | GCC | CCT | GTG | AAG | CGA | GCA | TCT | 576 |
| Glu | Leu | Phe | Ile | Leu | Ser | Thr | Thr | Glu | Ala | Pro | Val | Lys | Arg | Ala | Ser | |
| | | | 180 | | | | | 185 | | | | | 190 | | | |
| CTG | CTG | GGT | GAT | ATG | CAT | TTC | CGA | AGC | CTG | CGC | ACC | AAA | CTG | CTA | CTT | 624 |
| Leu | Leu | Gly | Asp | Met | His | Phe | Arg | Ser | Leu | Arg | Thr | Lys | Leu | Leu | Leu | |
| | | 195 | | | | | 200 | | | | | 205 | | | | |
| ATG | TCC | CGC | AAT | GAA | GAA | GCT | ACC | AAG | CAC | CTA | GAG | ACA | AGC | AAG | CAG | 672 |
| Met | Ser | Arg | Asn | Glu | Glu | Ala | Thr | Lys | His | Leu | Glu | Thr | Ser | Lys | Gln | |
| | 210 | | | | | 215 | | | | | 220 | | | | | |
| TTG | GCA | GCA | GCC | TTC | CAA | GAG | GAG | TTC | ACA | GTG | CGA | GAG | GAC | CTG | ATG | 720 |
| Leu | Ala | ALa | Ala | Phe | Gln | Glu | Glu | Phe | Thr | Val | Arg | Glu | Asp | Leu | Met | |
| 225 | | | | | 230 | | | | | 235 | | | | | 240 | |
| GGA | CTG | GCA | ATT | GGG | ACT | CAC | GGT | GCC | AAC | ATC | CAG | CAG | GCC | CGA | AAA | 768 |
| Gly | Leu | Ala | Ile | Gly | Thr | His | Gly | Ala | Asn | Ile | Gln | Gln | Ala | Arg | Lys | |
| | | | | 245 | | | | 250 | | | | | 255 | | | |
| GTA | CCT | GGG | GTG | ACC | GCC | ATT | GAG | TTG | GGT | GAA | GAG | ACC | TGC | ACT | TTC | 816 |
| Val | Pro | Gly | Val | Thr | Ala | Ile | Glu | Leu | Gly | Glu | Glu | Thr | Cys | Thr | Phe | |
| | | | 260 | | | | | 265 | | | | | 270 | | | |
| CGC | ATC | TAT | GGG | GAG | ACT | CCC | GAG | GCT | TGC | CGA | CAG | GCC | CGA | AGC | TAC | 864 |
| Arg | Ile | Tyr | Gly | Glu | Thr | Pro | Glu | Ala | Cys | Arg | Gln | Ala | Arg | Ser | Tyr | |
| | | 275 | | | | | 280 | | | | | 285 | | | | |
| CTT | GAG | TTT | TCT | GAG | GAC | TCA | GTG | CAA | GTG | CCC | AGG | AAC | CTG | GTT | GGC | 912 |
| Leu | Glu | Phe | Ser | Glu | Asp | Ser | Val | Gln | Val | Pro | Arg | Asn | Leu | Val | Gly | |
| | 290 | | | | | 295 | | | | | 300 | | | | | |
| AAA | GTG | ATT | GGA | AAG | AAC | GGG | AAA | GTG | ATC | CAG | GAG | ATT | GTG | GAT | AAA | 960 |
| Lys | Val | Ile | Gly | Lys | Asn | Gly | Lys | Val | Ile | Gln | Glu | Ile | Val | Asp | Lys | |
| 305 | | | | | 310 | | | | | 315 | | | | | 320 | |
| TCT | GGT | GTG | GTG | AGG | GTT | CGA | GTG | GAA | GGT | GAT | AAT | GAC | AAG | AAG | AAC | 1008 |
| Ser | Gly | Val | Val | Arg | Val | Arg | Val | Glu | Gly | Asp | Asn | Asp | Lys | Lys | Asn | |
| | | | | 325 | | | | | 330 | | | | | 335 | | |
| CCC | AGG | GAG | GAG | GGA | ATG | GTT | CCC | TTC | ATT | TTT | GTT | GGC | ACC | CGA | GAG | 1056 |
| Pro | Arg | Glu | Glu | Gly | Met | Val | Pro | Phe | Ile | Phe | Val | Gly | Thr | Arg | Glu | |
| | | | 340 | | | | | 345 | | | | | 350 | | | |
| AAC | ATC | AGC | AAT | GCC | CAG | GCT | TTG | CTG | GAG | TAT | CAC | CTC | TCC | TAC | CTG | 1104 |
| Asn | Ile | Ser | Asn | Ala | Gln | Ala | Leu | Leu | Glu | Tyr | His | Leu | Ser | Tyr | Leu | |
| | | 355 | | | | | 360 | | | | | 365 | | | | |
| CAG | GAG | GTA | GAG | CAG | CTT | CGC | TTG | GAG | AGG | CTA | CAA | ATT | GAT | GAG | CAG | 1152 |
| Gln | Glu | Val | Glu | Gln | Leu | Arg | Leu | Glu | Arg | Leu | Gln | Ile | Asp | Glu | Gln | |
| | 370 | | | | | 375 | | | | | 380 | | | | | |
| CTT | CGG | CAG | ATT | GGG | CTG | GGC | TTT | CGC | CCT | CCT | GGG | AGT | GGG | CGG | GGC | 1200 |
| Leu | Arg | Gln | Ile | Gly | Leu | Gly | Phe | Arg | Pro | Pro | Gly | Ser | Gly | Arg | Gly | |
| 385 | | | | | 390 | | | | | 395 | | | | | 400 | |
| AGC | GGT | GGC | AGC | GAC | AAG | GCT | GGA | TAT | AGC | ACT | GAT | GAG | AGC | TCC | TCC | 1248 |
| Ser | Gly | Gly | Ser | Asp | Lys | Ala | Gly | Tyr | Ser | Thr | Asp | Glu | Ser | Ser | Ser | |
| | | | | 405 | | | | | 410 | | | | | 415 | | |
| TCC | TCC | CTC | CAT | GCG | ACT | CGA | ACC | TAT | GGG | GGC | AGT | TAT | GGG | GGC | CGT | 1296 |
| Ser | Ser | Leu | His | Ala | Thr | Arg | Thr | Tyr | Gly | Gly | Ser | Tyr | Gly | Gly | Arg | |
| | | | 420 | | | | | 425 | | | | | 430 | | | |
| GGC | CGT | GGC | CGG | AGG | ACA | GGC | GGT | CCT | GCC | TAT | GGC | CCC | AGC | TCA | GAT | 1344 |
| Gly | Arg | Gly | Arg | Arg | Thr | Gly | Gly | Pro | Ala | Tyr | Gly | Pro | Ser | Ser | Asp | |
| | | 435 | | | | | 440 | | | | | 445 | | | | |
| GTG | TCT | ACA | GCT | TCA | GAG | ACT | GAG | TCA | GAG | AAG | AGA | GAG | GAG | CCC | AAC | 1392 |
| Val | Ser | Thr | Ala | Ser | Glu | Thr | Glu | Ser | Glu | Lys | Arg | Glu | Glu | Pro | Asn | |
| | 450 | | | | | 455 | | | | | 460 | | | | | |

| | | | | | | | | | | | | | | | |
|---|---|---|---|---|---|---|---|---|---|---|---|---|---|---|---|
|CGA|GCT|GGG|CCT|GGC|GAC|AGG|GAT|CCC|CCA|ACC|CGA|GGG|GAA|GAA|AGC|
|Arg|Ala|Gly|Pro|Gly|Asp|Arg|Asp|Pro|Pro|Thr|Arg|Gly|Glu|Glu|Ser|
|465| | | |470| | | | |475| | | | | |480|

1440

CGG AGG CGG CCG ACT GGG GGC CGG GGT AGG GGA CCC CCA CCT GCC CCC 1488
Arg Arg Arg Pro Thr Gly Gly Arg Gly Arg Gly Pro Pro Pro Ala Pro
                    485                     490                     495

CGG CCC ACT TCG AGA TAC AAT TCT TCA TCT ATT AGC TCA GTG CTG AAG 1536
Arg Pro Thr Ser Arg Tyr Asn Ser Ser Ser Ile Ser Ser Val Leu Lys
                500                     505                     510

GAT CCA GAC AGT AAT CCC TAC AGC CTA TTG GAC ACG TCT GAA CCA GAG 1584
Asp Pro Asp Ser Asn Pro Tyr Ser Leu Leu Asp Thr Ser Glu Pro Glu
            515                     520                     525

CCC CCG GTT GAT TCA GAA CCT GGG GAA CCC CCC CCA GCA AGT GCC AGG 1632
Pro Pro Val Asp Ser Glu Pro Gly Glu Pro Pro Pro Ala Ser Ala Arg
    530                     535                     540

CGC CGC CGC TCC CGC CGC CGC ACT GAT GAA GAC AGG ACC GTC ATG 1680
Arg Arg Arg Ser Arg Arg Arg Thr Asp Glu Asp Arg Thr Val Met
545                     550                     555                 560

GAT GGA GGC CTG GAA TCA GAT GGG CCC AAC ATG ACA GAG AAT GGC CTG 1728
Asp Gly Gly Leu Glu Ser Asp Gly Pro Asn Met Thr Glu Asn Gly Leu
                565                     570                     575

GAA GAT GAA TCA AGA CCT CAA CGT CGT AAT CGC AGC CGC CGC CGC CGT 1776
Glu Asp Glu Ser Arg Pro Gln Arg Arg Asn Arg Ser Arg Arg Arg Arg
            580                     585                     590

AAC CGT GGT AAT CGG ACT GAT GGC TCT ATC AGT GGA GAC CGC CAG CCA 1824
Asn Arg Gly Asn Arg Thr Asp Gly Ser Ile Ser Gly Asp Arg Gln Pro
        595                     600                     605

GTG ACT GTG GCT GAC TAT ATC TCA CGA GCA GAG TCT CAG AGC CGC CAG 1872
Val Thr Val Ala Asp Tyr Ile Ser Arg Ala Glu Ser Gln Ser Arg Gln
    610                     615                     620

AGC GCA CCC CTG GAA CGC ACT AAA CCC TCA GAA GAC TCT CTT TCA GGA 1920
Ser Ala Pro Leu Glu Arg Thr Lys Pro Ser Glu Asp Ser Leu Ser Gly
625                     630                     635                 640

CAG AAG GGT GAC TCT GTC AGC AAG CTT CCT AAG GGC CCC TCG GAG AAT 1968
Gln Lys Gly Asp Ser Val Ser Lys Leu Pro Lys Gly Pro Ser Glu Asn
                645                     650                     655

GGG GAG CTC TCC GCC CCC TTG GAG TTG GGT AGT ATG GTG AAT GGG GTT 2016
Gly Glu Leu Ser Ala Pro Leu Glu Leu Gly Ser Met Val Asn Gly Val
            660                     665                     670

TCA 2019
Ser (2) INFORMATION FOR SEQ ID NO:6:

(i) SEQUENCE CHARACTERISTICS:
        (A) LENGTH: 673 amino acid residues
        (B) TYPE: amino acid
        (C) STRANDEDNESS:
        (D) TOPOLOGY: linear (xi) SEQUENCE DESCRIPTION: SEQ ID NO:6:

Met Gly Gly Leu Ala Ser Gly Gly Asp Val Glu Pro Gly Leu Pro Val
1               5                   10                  15

Glu Val Arg Gly Ser Asn Gly Ala Phe Tyr Lys Gly Phe Val Lys Asp
                20                  25                  30

Val His Glu Asp Ser Val Thr Ile Phe Phe Glu Asn Asn Trp Gln Ser
            35                  40                  45

Glu Arg Gln Ile Pro Phe Gly Asp Val Arg Thr Pro Pro Pro Ala Asp
        50                  55                  60

Tyr Asn Lys Glu Ile Thr Glu Gly Asp Glu Val Glu Val Tyr Ser Arg
65                  70                  75                  80

```
Ala Asn Glu Gln Glu Pro Cys Gly Trp Trp Thr Ala Arg Val Arg Met
                85                  90                      95
Met Lys Gly Asp Phe Tyr Val Ile Glu Tyr Ala Ala Cys Asp Ala Thr
            100             105             110
Tyr Asn Glu Ile Val Thr Leu Glu Arg Leu Arg Pro Val Asn Pro Asn
        115             120             125
Pro Leu Ala Thr Lys Gly Ser Phe Phe Lys Val Thr Met Ala Val Pro
    130             135             140
Glu Asp Leu Arg Glu Ala Cys Ser Asn Glu Asn Val His Lys Glu Phe
145             150             155                     160
Lys Lys Ala Thr Gly Ala Asn Cys Ile Phe Thr Asn Ile Thr Asn Ser
            165             170             175
Glu Leu Phe Ile Leu Ser Thr Thr Glu Ala Pro Val Lys Arg Ala Ser
            180             185             190
Leu Leu Gly Asp Met His Phe Arg Ser Leu Arg Thr Lys Leu Leu Leu
        195             200             205
Met Ser Arg Asn Glu Glu Ala Thr Lys His Leu Glu Thr Ser Lys Gln
    210             215             220
Leu Ala ALa Ala Phe Gln Glu Glu Phe Thr Val Arg Glu Asp Leu Met
225             230             235                     240
Gly Leu Ala Ile Gly Thr His Gly Ala Asn Ile Gln Gln Ala Arg Lys
            245             250             255
Val Pro Gly Val Thr Ala Ile Glu Leu Gly Glu Glu Thr Cys Thr Phe
            260             265             270
Arg Ile Tyr Gly Glu Thr Pro Glu Ala Cys Arg Gln Ala Arg Ser Tyr
        275             280             285
Leu Glu Phe Ser Glu Asp Ser Val Gln Val Pro Arg Asn Leu Val Gly
    290             295             300
Lys Val Ile Gly Lys Asn Gly Lys Val Ile Gln Glu Ile Val Asp Lys
305             310             315                     320
Ser Gly Val Val Arg Val Arg Val Glu Gly Asp Asn Asp Lys Lys Asn
            325             330             335
Pro Arg Glu Glu Gly Met Val Pro Phe Ile Phe Val Gly Thr Arg Glu
            340             345             350
Asn Ile Ser Asn Ala Gln Ala Leu Leu Glu Tyr His Leu Ser Tyr Leu
        355             360             365
Gln Glu Val Glu Gln Leu Arg Leu Glu Arg Leu Gln Ile Asp Glu Gln
    370             375             380
Leu Arg Gln Ile Gly Leu Gly Phe Arg Pro Pro Gly Ser Gly Arg Gly
385             390             395                     400
Ser Gly Gly Ser Asp Lys Ala Gly Tyr Ser Thr Asp Glu Ser Ser Ser
            405             410             415
Ser Ser Leu His Ala Thr Arg Thr Tyr Gly Gly Ser Tyr Gly Gly Arg
            420             425             430
Gly Arg Gly Arg Arg Thr Gly Gly Pro Ala Tyr Gly Pro Ser Ser Asp
        435             440             445
Val Ser Thr Ala Ser Glu Thr Glu Ser Glu Lys Arg Glu Glu Pro Asn
    450             455             460
Arg Ala Gly Pro Gly Asp Arg Asp Pro Pro Thr Arg Gly Glu Glu Ser
465             470             475                     480
Arg Arg Arg Pro Thr Gly Gly Arg Gly Arg Gly Pro Pro Pro Ala Pro
            485             490             495
Arg Pro Thr Ser Arg Tyr Asn Ser Ser Ser Ile Ser Ser Val Leu Lys
```

|       |       |       | 500   |       |       |       | 505   |       |       |       | 510   |       |       |
|-------|-------|-------|-------|-------|-------|-------|-------|-------|-------|-------|-------|-------|-------|
| Asp   | Pro   | Asp   | Ser   | Asn   | Pro   | Tyr   | Ser   | Leu   | Leu   | Asp   | Thr   | Ser   | Glu   | Pro | Glu |

Asp Pro Asp Ser Asn Pro Tyr Ser Leu Leu Asp Thr Ser Glu Pro Glu
            515                 520                 525

Pro Pro Val Asp Ser Glu Pro Glu Pro Pro Ala Ser Ala Arg
    530             535             540

Arg Arg Arg Ser Arg Arg Arg Thr Asp Glu Asp Arg Thr Val Met
545             550             555                 560

Asp Gly Gly Leu Glu Ser Asp Gly Pro Asn Met Thr Glu Asn Gly Leu
            565             570                     575

Glu Asp Glu Ser Arg Pro Gln Arg Arg Asn Arg Ser Arg Arg Arg Arg
        580                 585             590

Asn Arg Gly Asn Arg Thr Asp Gly Ser Ile Ser Gly Asp Arg Gln Pro
        595             600             605

Val Thr Val Ala Asp Tyr Ile Ser Arg Ala Glu Ser Gln Ser Arg Gln
    610             615             620

Ser Ala Pro Leu Glu Arg Thr Lys Pro Ser Glu Asp Ser Leu Ser Gly
625             630             635                     640

Gln Lys Gly Asp Ser Val Ser Lys Leu Pro Lys Gly Pro Ser Glu Asn
            645             650             655

Gly Glu Leu Ser Ala Pro Leu Glu Leu Gly Ser Met Val Asn Gly Val
            660             665             670

Ser ( 2 ) INFORMATION FOR SEQ ID NO:7:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

GATGACATTT CTAAGCTACA GC        22

( 2 ) INFORMATION FOR SEQ ID NO:8:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

TGTACAAGCA CTATTGTAAA TG        22

( 2 ) INFORMATION FOR SEQ ID NO:9:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

CAGGGTCATA CCCCCTCC        18

( 2 ) INFORMATION FOR SEQ ID NO:10:

( i ) SEQUENCE CHARACTERISTICS:
        ( A ) LENGTH: 20 bases
        ( B ) TYPE: nucleic acid
        ( C ) STRANDEDNESS: single -continued (D) TOPOLOGY: linear (xi) SEQUENCE DESCRIPTION: SEQ ID NO:10:

CTGAACGGTC AAATCTGGGT    20

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Arg Arg Arg Arg Ser Arg Arg Arg Arg
1               5

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Gly Lys Arg Cys Asp
1               5

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa at 4 is Ser or Pro"

(xi) SEQUENCE DESCRIPTION: SEQ ID NO:13:

Asn Gly Val Xaa
1